United States Patent
Strong et al.

(10) Patent No.: US 10,647,679 B2
(45) Date of Patent: May 12, 2020

(54) N-METHYL-D-ASPARTATE RECEPTOR (NMDAR) POTENTIATORS, PHARMACEUTICAL COMPOSITIONS, AND USES RELATED THERETO

(71) Applicant: Emory University, Atlanta, GA (US)

(72) Inventors: Katie L. Strong, Atlanta, GA (US); David Menaldino, Atlanta, GA (US); Dennis C. Liotta, Atlanta, GA (US); Stephen F. Traynelis, Decatur, GA (US); Rose M. Freel, Mariottsville, MD (US); Matthew Epplin, Atlanta, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 15/558,971

(22) PCT Filed: Mar. 15, 2016

(86) PCT No.: PCT/US2016/022430
§ 371 (c)(1),
(2) Date: Sep. 15, 2017

(87) PCT Pub. No.: WO2016/149248
PCT Pub. Date: Sep. 22, 2016

(65) Prior Publication Data
US 2018/0244623 A1 Aug. 30, 2018

Related U.S. Application Data

(60) Provisional application No. 62/133,438, filed on Mar. 15, 2015.

(51) Int. Cl.
| | | |
|---|---|---|
| *C07D 217/16* | (2006.01) | |
| *C07D 409/06* | (2006.01) | |
| *C07D 413/06* | (2006.01) | |
| *C07D 417/06* | (2006.01) | |
| *C07D 407/06* | (2006.01) | |
| *C07D 405/06* | (2006.01) | |

(52) U.S. Cl.
CPC ......... *C07D 217/16* (2013.01); *C07D 405/06* (2013.01); *C07D 407/06* (2013.01); *C07D 409/06* (2013.01); *C07D 413/06* (2013.01); *C07D 417/06* (2013.01); *C07B 2200/07* (2013.01)

(58) Field of Classification Search
CPC .. C07D 217/06; C07D 405/06; C07D 407/06; C07D 409/06; C07D 413/06; C07D 417/06
See application file for complete search history.

(56) References Cited

U.S. PATENT DOCUMENTS

| | | | | |
|---|---|---|---|---|
| 7,067,507 | B2* | 6/2006 | Pulley | C07D 273/02 514/183 |
| 8,835,438 | B2 | 9/2014 | Ishiyama | |
| 2002/0197233 | A1 | 12/2002 | Relton | |
| 2005/0153998 | A1 | 7/2005 | Ito | |
| 2008/0234317 | A1 | 9/2008 | Kleemann | |
| 2009/0209528 | A1 | 8/2009 | Mas Prio | |
| 2012/0028977 | A1 | 2/2012 | Traynelis | |
| 2013/0316954 | A1 | 11/2013 | Moskal | |
| 2013/0331394 | A1 | 12/2013 | Siekmeier | |
| 2014/0275529 | A1* | 9/2014 | Traynelis | C07D 209/08 544/128 |

FOREIGN PATENT DOCUMENTS

| | | | |
|---|---|---|---|
| WO | 1996011698 | 4/1996 | |
| WO | 2007006157 | 1/2007 | |
| WO | 2007050124 | 5/2007 | |
| WO | WO 2010088414 | * 8/2010 | ........... C07D 217/04 |

OTHER PUBLICATIONS

Zawilska. Pharmacological Reports, 2004, 65, 1-14 (Year: 2004).*
Humber. Canadian Journal of Chemistry, 1971, 49(6), 857-62. (Year: 1971).*
Acker et al., Mechanism for Noncompetitive Inhibition by Novel GluN2C/D N-Methyl-D-Aspartate Receptor Subunit-Selective Modulators, Molecular Pharmacology, 2011, 80 (5), pp. 782-795.
Brigman et al., Loss of GluN2b_Containing NMDA Receptors in CA1 Hippocampus and Cortex Impairs Long-Term Depression, Reduces Dendritic Spine Density, and Disrupts Learning, Journal of Neuroscience, 2010, 30 (13), pp. 4590-4600.
Hardingham et al., Synaptic versus Extrasynaptic NMDA Receptor Signalling: Implications for Neurodegenerative Disorders, Nature Reviews Neuroscience, 2010, 11, pp. 682-696.
Ogden et al. New advances in NMDA receptor pharmacology, Trends in Pharmacological Sciences Dec. 2011, vol. 32, No. 12, 726-733.
Ogden et al. Contribution of the M1 Transmembrane Helix and Pre-M1 Region to Positive Allosteric Modulation and Gating of N-Methyl-D-Aspartate Receptors, Mol Pharmacol 83:1045-1056, 2013.
Santangelo et al., Synthesis and Structure Activity Relationship of Tetrahydroquinoline-Based Potentiators of GluN2C and GluN2D Containing N-Methyl-D-Aspartate Receptors, Journal of Medicinal Chemistry, 2013, 56 (13), pp. 5351-5381.

(Continued)

*Primary Examiner* — Noble E Jarrell
(74) *Attorney, Agent, or Firm* — Emory Patent Group

(57) ABSTRACT

This disclosure relates to tetrahydroisoquinolines, salts, and derivatives useful for managing mental or cognitive diseases or conditions of the brain or central nervous system. In certain embodiments, the disclosure relates to compounds and compositions having formula I: prodrugs, esters, or salts thereof, wherein the substituents are described herein.

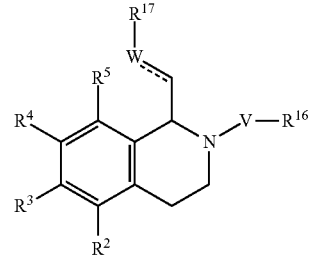

Formula I

12 Claims, 8 Drawing Sheets

(56) References Cited

OTHER PUBLICATIONS

Strong et al. The Structure-Activity Relationship of a Tetrahydroisoquinoline Class of N-Methyl-D-Aspartate Receptor Modulators that Potentiates GluN2B-Containing N-Methyl-D-Aspartate Receptors, J. Med. Chem. 2017, 60, 5556-5585.
Suryavanshi et al. GluN2C/GluN2D subunit-selective NMDA receptor potentiator CIQ reverses MK-801-induced impairment in prepulse inhibition and working memory in Y-maze test in mice, British Journal of Pharmacology (2014) 171 799-809 799.
Tang et al., Genetic Enhancement of Learning and Memory in Mice, Nature, 1999, 401, pp. 63-69.
Traynelis et al., Glutamate Receptor Ion Channels: Structure, Regulation, and Function, Pharmacological Reviews, 2010, 62 (3), pp. 405-496.
Zimmerman et al., Design, Synthesis, and Structure-Activity Relationship of a Novel Series of GluN2C-Selective Potentiators, Journal of Medicinal Chemistry, 2014, 57 (6), pp. 2334-2356.

\* cited by examiner

| Structure | Activity | Structure | Activity |
|---|---|---|---|
|  | GluN2C = 4.9 (253%)<br>GluN2D = 5.5 (287%) |  | GluN2C = 11 (186%)<br>GluN2D = 14 (188%) |
|  | GluN2C = 184% at 30 μM<br>GluN2D = 222% at 30 μM |  | GluN2C = 7.0 (254%)<br>GluN2D = 9.0 (295%) |
|  | GluN2C = 0.9 (147%)<br>GluN2D = 1.0 (149%) |  | GluN2C = 148% at 30 μM<br>GluN2D = 150% at 30 μM |
|  | GluN2D = 131% at 30 μM |  | GluN2C = 15 (291%)<br>GluN2D = 23 (344%) |
|  | GluN2D = 223% at 100 μM | | |

N-METHYL-D-ASPARTATE RECEPTOR (NMDAR) POTENTIATORS, PHARMACEUTICAL COMPOSITIONS, AND USES RELATED THERETO

CROSS-REFERENCE TO RELATED APPLICATIONS

This application is the National Stage of International Application Number PCT/US2016/022430 filed Mar. 15, 2016, which claims priority to U.S. Provisional Application No. 62/133,438 filed Mar. 15, 2015. The entirety of each of these applications is hereby incorporated by reference for all purposes.

CROSS REFERENCE TO RELATED APPLICATION

This Application Claims priority to U.S. Provisional Application No. 62/133,438 filed Mar. 15, 2015, hereby incorporated by reference in its entirety.

BACKGROUND

NMDARs typically contain a GluN1 subunit in addition to GluN2A-GluN2D subunits. Stimulation of one or more of the subunits are thought to be beneficial for the treatment of cognitive dysfunctions as well as other conditions dependent on synaptic plasticity such as motor retraining and rehabilitation after ischemic insult, traumatic brain injury, and conditions that involve impairment of movement, speech, vision, or other functions controlled by the brain. See Traynelis et al., Glutamate receptor ion channels: structure, regulation, and function. Pharmacol Rev, 2010, 62:405-496. See also Hardingham & Bading, Synaptic versus extrasynaptic NMDA receptor signaling: implications for neurodegenerative disorders, Nat Rev, Neurosci, 2010; 11:682-696; Tang et al., Genetic enhancement of learning and memory in mice, Nature, 401, 63-69 (1999); and Brigman et al., Loss of GluN2B-containing NMDA receptors in CA1 hippocampus and cortex impairs long-term depression, reduces dendritic spine density, and disrupts learning. J Neurosci, 2010, 30, 4590-4600.

Tetrahydroisoquinoline-based potentiators of GluN2C and GluN2D containing N-methyl-D-aspartate receptors are reported in Santangelo et al., J Med Chem, 2013, 56(13): 5351-81. See also US Published Application 2014/0275529; US 2012/0028977; Acker et al., Mol Pharmacol, 2011, 80(5):782-95; and Zimmerman et al., J Med Chem, 2014, 57(6):2334-56.

References cited herein are not an admission of prior art.

SUMMARY

This disclosure relates to tetrahydroisoquinolines, salts, and derivatives useful for managing mental or cognitive diseases or conditions of the brain or central nervous system. In certain embodiments, the disclosure relates to compounds and compositions having formula I:

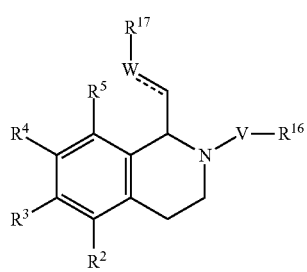

Formula I prodrugs, esters, or salts thereof, wherein the substituents are described herein.

In certain embodiments, the disclosure relates to pharmaceutical compositions comprising a compound as reported herein and a pharmaceutically acceptable excipient.

In certain embodiments, the disclosure relates to methods of treating or preventing a neurological disease, condition, or disorder comprising administering an effective amount of a compound disclosed herein to a subject in need thereof. In certain embodiments, the condition is depression, anxiety, schizophrenia, or bipolar disorder.

In certain embodiments, the condition is a central nervous system (CNS) disorders such as those selected from Alzheimer's disease, Huntington's disease, and Amyotrophic Lateral Sclerosis (ALS). In certain embodiments, the disclosure relates to methods of improving learning or memory comprising administering an effective amount of a compound disclosed herein to a subject in need thereof.

In certain embodiments, the disclosure relates to methods of improving recovery and retraining after a CNS injury comprising administering an effective amount of a compound disclosed herein to a subject in need thereof. In certain embodiments, the CNS injury is traumatic brain injury, stroke, hypoxia, cognitive deficits following coronary artery bypass grafting, and spinal cord injury.

DETAILED DESCRIPTION

Figure 1A:
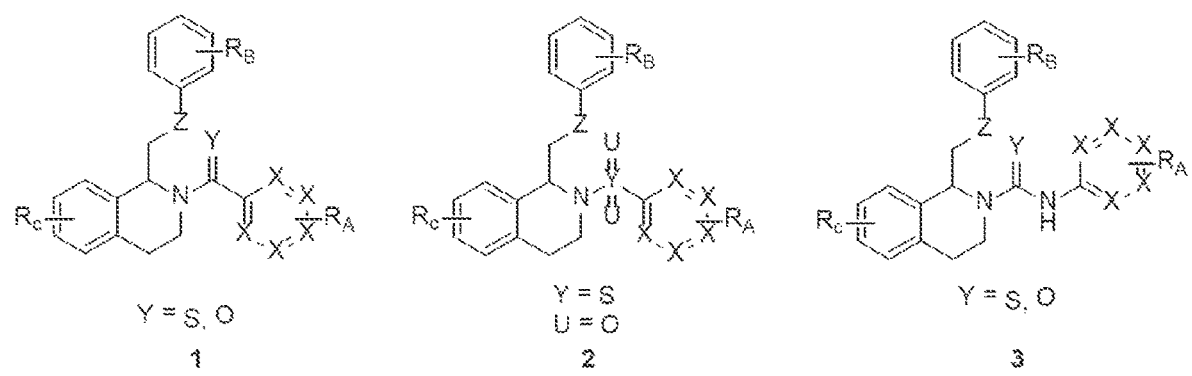
FIG. 1A illustrates certain embodiments disclosed herein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers to an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "thiophenyl" refers to the five-membered heteroaryl having one sulfur heteroatom.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, and t-butoxy.

"Alkylamino" refers to an alkyl group as defined above attached through an amino bridge. An example of an alkylamino is methylamino, (i.e., —NH—CH$_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

"Aminoalkyl" refers to an amino group attached through an alkyl bridge. An example of an aminoalkyl is aminomethyl, (i.e., NH$_2$—CH$_2$—).

"Hydroxyalkyl" refers to a hydroxy group attached through an alkyl bridge. An example of a hydroxyalkyl is hydroxyethyl, (i.e., HO—CH$_2$CH$_2$—).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers to any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

Tetrahydroisoquinoline Derivatives

In certain embodiments, the disclosure relates to tetrahydroisoquinoline derivatives for uses reported herein. In certain embodiments, the tetrahydroisoquinoline derivatives have formula I:

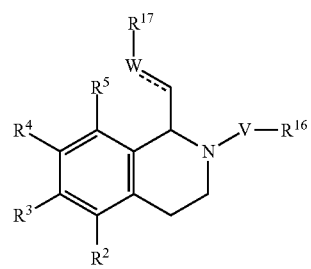

Formula I prodrugs or salts thereof, wherein:

V is C=S, C=O, SO$_2$, —(C=S)NH—, —(C=NH)S—, —(C=O)NH—, CH$_2$, or a single bond directly to R$^{16}$;

W is O, S, NH, CH$_2$, provided ═ is a single bond or W is CH provided ═ is a double bond;

R$^2$, R$^3$, R$^4$, and R$^5$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^2$, R$^3$, R$^4$, and R$^5$ are optionally substituted with one or more, the same or different, R$^{20}$;

R$^{16}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{16}$ is optionally substituted with one or more, the same or different, R$^{20}$;

R$^{17}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{17}$ is optionally substituted with one or more, the same or different, R$^{20}$;

R$^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{20}$ is optionally substituted with one or more, the same or different, R$^{21}$; and R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dimethyl sulfamoyl, N,N-diethylsulfamoyl, N-methyl-N-ethylsulfamoyl, carbocyclyl, aryl, or heterocyclyl.

In certain embodiments, V is C=S or SO$_2$ and R$^4$ is hydrogen.

In certain embodiments, R$^3$ is (C$_{2-4}$)alkoxy, isopropoxy, (C$_{3-6}$)cycloalkyloxy, cyclopentyloxy, benzyloxy, benzylthio, 2-phenylethyloxy, 2-phenylethylthiol, alkylthiol, alkylamino, dialkylamino, morpholinyl, or piperidinyl.

In certain embodiments, V is C=O, C=S, or SO$_2$, R$^3$ is (C$_{2-4}$)alkoxy, isopropoxy, (C$_{3-6}$)cycloalkyloxy, cyclopentyloxy, benzyloxy, benzylthio, 2-phenylethyloxy, 2-phenylethylthiol, alkylthiol, alkylamino, dialkylamino, morpholinyl, or piperidinyl, and R$^4$ is hydrogen.

In certain embodiments, V is —(C=S)NH—, —(C=O)NH—, and R$^4$ is hydrogen.

In certain embodiments, V is —(C=S)NH— or —(C=O)NH—, R$^3$ is (C$_{2-4}$)alkoxy, isopropoxy, (C$_{3-6}$)cycloalkyloxy, cyclopentyloxy, benzyloxy, benzylthio, 2-phenylethyloxy, 2-phenylethylthio, alkylthio, alkylamino, dialkylamino, morpholinyl, or piperidinyl, and R$^4$ is hydrogen.

In certain embodiments, R$^{16}$ is thiophenyl, furanyl, thiazolyl, and oxazolyl which is optionally substituted.

In certain embodiments, R$^{16}$ is an alkyl or alkenyl substituted with one or more halogen.

In certain embodiments, R$^{16}$ is 2-chlorovin-1-yl, 4,4,4-trifluorobut-1-yl, 3,3,3-trifluoro-2-methylprop-1-en-1-yl, or 3,3,3-trifluoroprop-1-en-1-yl.

In certain embodiments, R$^{17}$ is thiophenyl.

In certain embodiments, V is C=S.

In certain embodiments, V is SO$_2$,

In certain embodiments, V is —(C=S)NH— or —(C=NH)S—.

In certain embodiments, V is —(C=O)NH—.

In certain embodiments, V is CH$_2$.

In certain embodiments, V is a single bond directly to R$^{16}$ wherein R$^{16}$ is phenyl, heterocyclyl, five-membered heterocyclyl, or thiophenyl, furanyl, thiazolyl, and oxazolyl which is optionally substituted.

In certain embodiments, V is C=S or SO$_2$.

In certain embodiments, V is C=S or SO$_2$ and R$^3$ is hydroxy, alkoxy, alkylamino, dialkylamino, morpholinyl, or piperidinyl.

In certain embodiments, V is —(C=S)NH—, —(C=NH)S—, or —(C=O)NH— and R$^3$ is hydroxy, alkoxy, alkylamino, dialkylamino, morpholinyl, or piperidinyl.

In certain embodiments, R$^{16}$ is thiophenyl, furanyl, thiazolyl, and oxazolyl which is optionally substituted.

In certain embodiments, V is C=S, W is O or S, and R$^{17}$ is optionally substituted phenyl.

In certain embodiments, V is SO$_2$, W is O or S, and R$^{17}$ is optionally substituted phenyl.

In certain embodiments, V is —(C=S)NH— or —(C=NH)S—, W is O or S, and R$^{17}$ is optionally substituted phenyl.

In certain embodiments, V is —(C=O)NH—, W is O or S, and R$^{17}$ is optionally substituted phenyl.

In certain embodiments, V is CH$_2$, W is O or S, and R$^{17}$ is optionally substituted phenyl.

In certain embodiments, V is a single bond directly to R$^{16}$ wherein R$^{16}$ is phenyl, heterocyclyl, five-membered heterocyclyl, or thiophenyl, furanyl, thiazolyl, and oxazolyl which is optionally substituted, W is O, and R$^{17}$ is optionally substituted phenyl.

In certain embodiments, V is C=O, W is O or S, R$^3$ is hydroxy, alkoxy, alkylamino, dialkylamino, morpholinyl, or piperidinyl, and R$^{17}$ is optionally substituted phenyl.

In certain embodiments, V is C=S, W is O or S, R$^3$ is hydroxy, alkoxy, alkylamino, dialkylamino, morpholinyl, or piperidinyl, and R$^{17}$ is optionally substituted phenyl.

In certain embodiments, V is SO$_2$, W is O or S, R$^3$ is hydroxy, alkoxy, alkylamino, dialkylamino, morpholinyl, or piperidinyl, and R$^{17}$ is optionally substituted phenyl.

In certain embodiments, V is —(C=S)NH—, W is O or S, R$^3$ is hydroxy, alkoxy, alkylamino, morpholinyl, or piperidinyl, and R$^{17}$ is optionally substituted phenyl.

In certain embodiments, V is —(C=S)NH— or —(C=NH)S—, W is O or S, R$^3$ is hydroxy, alkoxy, alkylamino, dialkylamino, morpholinyl, or piperidinyl, and R$^{17}$ is optionally substituted phenyl.

In certain embodiments, V is CH$_2$, W is O or S, R$^3$ is hydroxy, alkoxy, alkylamino, dialkylamino, morpholinyl, or piperidinyl, and R$^{17}$ is optionally substituted phenyl.

In certain embodiments, V is a single bond directly to R$^{16}$ wherein R$^{16}$ is phenyl, heterocyclyl, five-membered heterocyclyl, or thiophenyl, furanyl, thiazolyl, and oxazolyl, W is O or S, R$^3$ is hydroxy, alkoxy, alkylamino, dialkylamino, morpholinyl, or piperidinyl, and R$^{17}$ is optionally substituted phenyl.

In certain embodiments, the tetrahydroisoquinoline derivatives of formula I have formula IA:

Formula IA

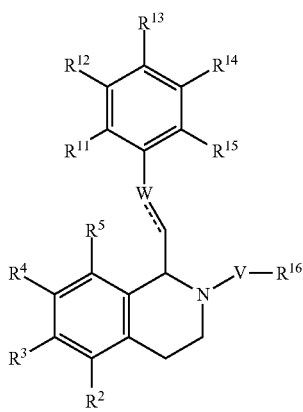

prodrugs or salts thereof, wherein:

V is C=S, C=O, SO$_2$, —(C=S)NH—, —(C=NH)S—, —(C=O)NH—, CH$_2$, or a single bond directly to R$^{16}$;

W is O, S, NH, CH$_2$, provided ⁼ is a single bond or W is CH provided ⁼ is a double bond;

R$^2$, R$^3$, R$^4$, R$^5$, R$^{11}$, R$^{12}$, R$^{13}$, R$^{14}$, and R$^{15}$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^2$, R$^3$, R$^4$, R$^5$, R$^{11}$, R$^{12}$, R$^{13}$, R$^{14}$, and R$^{15}$ are optionally substituted with one or more, the same or different, R$^{20}$;

R$^{16}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{16}$ is optionally substituted with one or more, the same or different, R$^{20}$;

R$^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{20}$ is optionally substituted with one or more, the same or different, R$^{21}$; and R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, V is C=S.
In certain embodiments, V is SO$_2$,
In certain embodiments, V is —(C=S)NH— or —(C=NH)S—.
In certain embodiments, V is —(C=O)NH—.
In certain embodiments, V is CH$_2$.

In certain embodiments, V is a single bond directly to R$^{16}$ wherein R$^{16}$ is phenyl, heterocyclyl, five-membered heterocyclyl, or thiophenyl, furanyl, thiazolyl, and oxazolyl which is optionally substituted.

In certain embodiments, V is C=S and W is O or S.
In certain embodiments, V is SO$_2$ and W is O or S.
In certain embodiments, V is —(C=S)NH— or —(C=NH)S—, and W is O or S.
In certain embodiments, V is —(C=O)NH— and W is O or S.
In certain embodiments, V is CH$_2$ and W is O or S.
In certain embodiments, V is a single bond directly to R$^{16}$ wherein R$^{16}$ is phenyl, heterocyclyl, five-membered heterocyclyl, or thiophenyl, furanyl, thiazolyl, and oxazolyl, and W is O or S.

In certain embodiments, V is C=O, W is O, and R$^3$ is hydroxy, alkoxy, alkylamino, dialkylamino, morpholinyl, or piperidinyl.

In certain embodiments, V is C=S, W is O or S, and R$^3$ is hydroxy, alkoxy, alkylamino, dialkylamino, morpholinyl, or piperidinyl.

In certain embodiments, V is SO$_2$, W is O or S, and R$^3$ is hydroxy, alkoxy, alkylamino, dialkylamino, morpholinyl, or piperidinyl.

In certain embodiments, V is —(C=S)NH— or —(C=NH)S—, W is O or S, and R$^3$ is hydroxy, alkoxy, alkylamino, dialkylamino, morpholinyl, or piperidinyl.

In certain embodiments, V is —(C=O)NH—, W is O or S, and R$^3$ is hydroxy, alkoxy, alkylamino, morpholinyl, or piperidinyl.

In certain embodiments, V is CH$_2$, W is O or S, and R$^3$ is hydroxy, alkoxy, alkylamino, dialkylamino, morpholinyl, or piperidinyl.

In certain embodiments, V is a single bond directly to R$^{16}$ wherein R$^{16}$ is phenyl, heterocyclyl, five-membered heterocyclyl, or thiophenyl, furanyl, thiazolyl, and oxazolyl, W is O or S, and R$^3$ is hydroxy, alkoxy, alkylamino, dialkylamino, morpholinyl, or piperidinyl.

In certain embodiments, with regard to any of the formula disclosed herein, R$^{11}$, R$^{12}$, R$^{14}$, and R$^{15}$ are hydrogen, or R$_{11}$ and R$^{15}$ are not alkoxy, methoxy, or ethoxy.

In certain embodiments, with regard to any of the formula disclosed herein, R$^{13}$ is hydrogen and R$^{15}$ is alkoxy, methoxy, or ethoxy which is optionally substituted.

In certain embodiments, with regard to any of the formula disclosed herein, R$^4$ is —O-benzoyl or —O-benzyl which is optionally substituted.

In certain embodiments, the tetrahydroisoquinoline derivatives of formula I have formula IB:

Formula IB

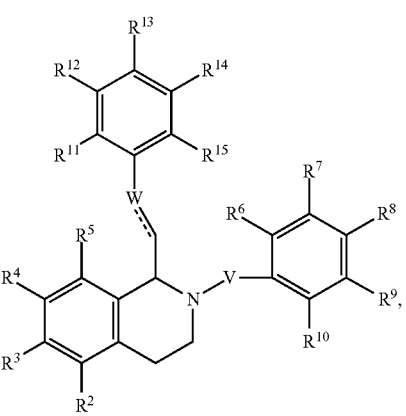

prodrugs or salts thereof, wherein:
V is C=S, C=O, SO$_2$, —(C=S)NH—, —(C=NH)S—, —(C=O)NH—, CH$_2$, or a single bond directly to R$^{16}$;

W is O, S, NH, CH$_2$, provided ⁑ is a single bond or W is CH provided ⁑ is a double bond;

R$^2$, R$^3$, R$^4$, R$^5$, R$^6$, R$^7$, R$^8$, R$^9$, R$^{10}$, R$^{11}$, R$^{12}$, R$^{13}$, R$^{14}$, and R$^{15}$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^2$, R$^3$, R$^4$, R$^5$, R$^6$, R$^7$, R$^8$, R$^9$, R$^{10}$, R$^{11}$, R$^{12}$, R$^{13}$, R$^{14}$, and R$^{15}$ are optionally substituted with one or more, the same or different, R$^{20}$;

R$^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{20}$ is optionally substituted with one or more, the same or different, R$^{21}$; and R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl.

In certain embodiments, V is C=S.
In certain embodiments, V is SO$_2$,
In certain embodiments, V is —(C=S)NH— or —(C=NH)S—.
In certain embodiments, V is —(C=O)NH—.
In certain embodiments, V is CH$_2$.
In certain embodiments, V is C=S and W is O or S.
In certain embodiments, V is SO$_2$ and W is O or S.
In certain embodiments, V is —(C=S)NH— and W is O or S.
In certain embodiments, V is —(C=O)NH— and W is O or S.
In certain embodiments, V is CH$_2$ and W is O or S.
In certain embodiments, W is O or S.
In certain embodiments, V is C=O, W is O or S, and R$^3$ is hydroxy, alkoxy, alkylamino, dialkylamino, morpholinyl, or piperidinyl.
In certain embodiments, V is C=S, W is O or S, and R$^3$ is hydroxy, alkoxy, alkylamino, dialkylamino, morpholinyl, or piperidinyl.
In certain embodiments, V is SO$_2$, W is O or S, and R$^3$ is hydroxy, alkoxy, alkylamino, dialkylamino, morpholinyl, or piperidinyl.
In certain embodiments, V is —(C=S)NH— or —(C=NH)S—, W is O or S, and R$^3$ is hydroxy, alkoxy, alkylamino, dialkylamino, morpholinyl, or piperidinyl.
In certain embodiments, V is —(C=O)NH—, W is O or S, and R$^3$ is hydroxy, alkoxy, alkylamino, dialkylamino, morpholinyl, or piperidinyl.
In certain embodiments, V is CH$_2$, W is O, and R$^3$ is hydroxy, alkoxy, alkylamino, dialkylamino, morpholinyl, or piperidinyl.

In certain embodiments, W is O or S and R$^3$ is hydroxy, alkoxy, alkylamino, dialkylamino, morpholinyl, or piperidinyl.
In certain embodiments, R$^7$ is halogen or halogenated alkyl.
In certain embodiments, R$^8$ is halogen or halogenated alkyl.
In certain embodiments, R$^7$ is halogen or halogenated alkyl and V is C=S or C=O.
In certain embodiments, R$^8$ is halogen or halogenated alkyl and V is C=S or C=O.
In certain embodiments, the tetrahydroisoquinoline derivatives of formula I have formula IC:

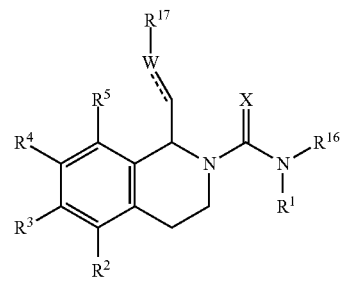

Formula IC prodrugs or salts thereof, wherein:
W is O, S, NH, CH$_2$, provided ⁑ is a single bond or W is CH provided ⁑ is a double bond;
X is O or S;
R$^1$ is hydrogen or alkyl, wherein R$^1$ is optionally substituted with one or more, the same or different, R$^{20}$
R$^2$, R$^3$, R$^4$, and R$^5$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^2$, R$^3$, R$^4$, and R$^5$ are optionally substituted with one or more, the same or different, R$^{20}$;
R$^{16}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{16}$ is optionally substituted with one or more, the same or different, R$^{20}$;
R$^{17}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{17}$ is optionally substituted with one or more, the same or different, R$^{20}$;
R$^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{20}$ is optionally substituted with one or more, the same or different, R$^{21}$; and
R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, W is O or S, and $R^{17}$ is optionally substituted phenyl.

In certain embodiments, $R^{16}$ is phenyl, heterocyclyl, five-membered heterocyclyl, or thiophenyl, furanyl, thiazolyl, and oxazolyl, W is O, and $R^{17}$ is optionally substituted phenyl.

In certain embodiments, W is O or S, $R^3$ is hydroxy, alkoxy, alkylamino, dialkylamino, morpholinyl, or piperidinyl, and $R^{17}$ is optionally substituted phenyl.

In certain embodiments, W is O or S, $R^3$ is hydroxy, alkoxy, alkylamino, dialkylamino, morpholinyl, or piperidinyl, and $R^{17}$ is optionally substituted phenyl.

In certain embodiments, W is O or S, $R^3$ is hydroxy, alkoxy, alkylamino, dialkylamino, morpholinyl, or piperidinyl, and $R^{17}$ is optionally substituted phenyl.

In certain embodiments, W is O or S, $R^3$ is hydroxy, alkoxy, alkylamino, dialkylamino, morpholinyl, or piperidinyl, and $R^{17}$ is optionally substituted phenyl.

In certain embodiments, W is O or S, $R^3$ is hydroxy, alkoxy, alkylamino, dialkylamino, morpholinyl, or piperidinyl, and $R^{17}$ is optionally substituted phenyl.

In certain embodiments, W is O or S, $R^3$ is hydroxy, alkoxy, alkylamino, dialkylamino, morpholinyl, or piperidinyl, and $R^{17}$ is optionally substituted phenyl.

In certain embodiments, $R^{16}$ is phenyl, heterocyclyl, five-membered heterocyclyl, or thiophenyl, furanyl, thiazolyl, and oxazolyl, W is O or S, $R^3$ is hydroxy, alkoxy, alkylamino, dialkylamino, morpholinyl, or piperidinyl, and $R^{17}$ is optionally substituted phenyl.

In certain embodiments, the tetrahydroisoquinoline derivatives of formula I have formula ID:

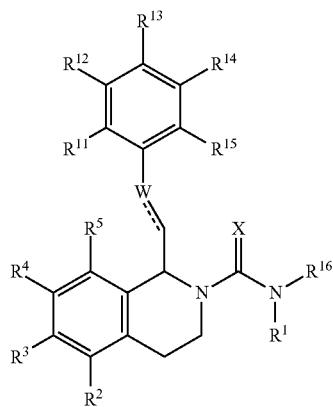

Formula ID prodrugs or salts thereof, wherein:

W is O, S, NH, $CH_2$, provided ═ is a single bond or W is CH provided ═ is a double bond;

X is O or S;

$R^1$ is hydrogen or alkyl, wherein $R^1$ is optionally substituted with one or more, the same or different, $R^{20}$ $R^2$, $R^3$, $R^4$, $R^5$, $R^{11}$, $R^{12}$, $R^{13}$, $R^{14}$, and $R^{15}$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^2$, $R^3$, $R^4$, $R^5$, $R^{11}$, $R^{12}$, $R^{13}$, $R^{14}$, and $R^{15}$ are optionally substituted with one or more, the same or different, $R^{20}$;

$R^{16}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^{16}$ is optionally substituted with one or more, the same or different, $R^{20}$;

$R^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl.

In certain embodiments, W is O or S.

In certain embodiments, W is O or S and $R^3$ is hydroxy, alkoxy, alkylamino, dialkylamino, morpholinyl, or piperidinyl.

In certain embodiments, $R^{16}$ is phenyl, heterocyclyl, five-membered heterocyclyl, or thiophenyl, furanyl, thiazolyl, and oxazolyl which is optionally substituted, W is O or S, and $R^3$ is hydroxy, alkoxy, alkylamino, dialkylamino, morpholinyl, or piperidinyl.

In certain embodiments, the tetrahydroisoquinoline derivatives of formula I have formula IE:

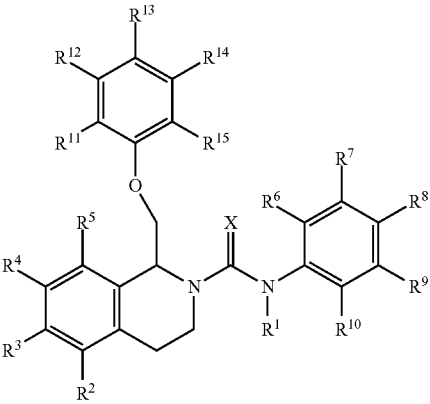

FIG. IE prodrugs or salts thereof, wherein:

X is O or S;

$R^1$ is hydrogen or alkyl, wherein $R^1$ is optionally substituted with one or more $R^{20}$;

$R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are optionally substituted with one or more, the same or different, $R^{20}$;

$R^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl.

In certain embodiments, $R^7$ is halogen or halogenated alkyl.

In certain embodiments, $R^8$ is halogen or halogenated alkyl.

In certain embodiments, the tetrahydroisoquinoline derivatives of formula I have formula IF:

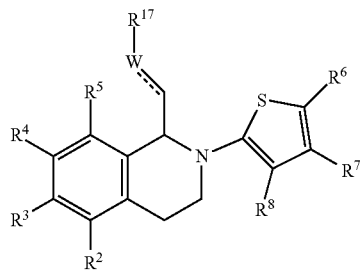

Formula IF prodrugs or salts thereof, wherein:

W is O, S, NH, CH$_2$, provided ═ is a single bond or W is CH provided ═ is a double bond;

$R^2$, $R^3$, $R^4$, $R^5$, $R^6$, $R^7$, and $R^8$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^2$, $R^3$, $R^4$, $R^5$, $R^6$, $R^7$, and $R^8$ are optionally substituted with one or more, the same or different, $R^{20}$;

$R^{17}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^{17}$ is optionally substituted with one or more, the same or different, $R^{20}$;

$R^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl.

In certain embodiments, the tetrahydroisoquinoline derivatives of formula I have formula IG:

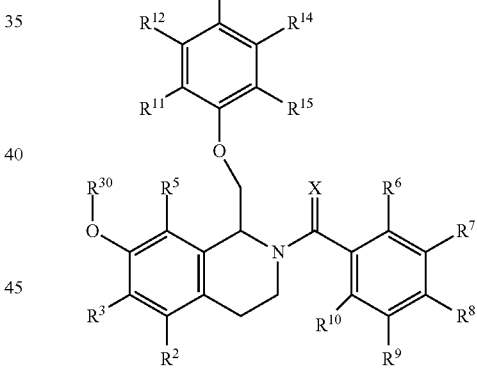

FIG. IG prodrugs or salts thereof, wherein:

X is O or S;

$R^1$ is hydrogen or alkyl, wherein $R^1$ is optionally substituted with one or more $R^{20}$;

$R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, aryl, or heterocyclyl, wherein $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are optionally substituted with one or more, the same or different, $R^{20}$;

$R^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, carbocyclyl, aryl, or heterocyclyl, wherein $R^{20}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl $R^{30}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkyl sulfinyl, alkyl sulfonyl, aryl sulfonyl, benzyl, benzoyl, carbocyclyl, aryl, or heterocyclyl, wherein $R^{30}$ is optionally substituted with one or more, the same or different, $R^{31}$; and $R^{31}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^3$ is alkoxy.

In certain embodiments, $R^{30}$ is hydrogen, benzyl, or benzoyl optionally substituted.

In certain embodiments, the tetrahydroisoquinoline derivatives of formula I have formula IH:

Formula IH

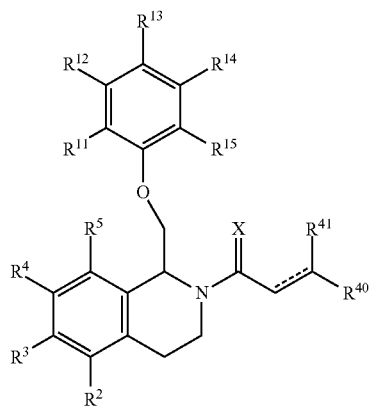

prodrugs or salts thereof, wherein:
the dotted line represents a double bond or single bond when absent;
X is O or S;

$R^1$ is hydrogen or alkyl, wherein $R^1$ is optionally substituted with one or more $R^{20}$;

$R^2$, $R^3$, $R^4$, $R^5$, $R^{11}$, $R^{12}$, $R^{13}$, $R^{14}$, and $R^{15}$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^2$, $R^3$, $R^4$, $R^5$, $R^{11}$, $R^{12}$, $R^{13}$, $R^{14}$, and $R^{15}$ are optionally substituted with one or more, the same or different, $R^{20}$;

$R^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein $R^{20}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl $R^{40}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, benzyl, benzoyl, carbocyclyl, aryl, or heterocyclyl, wherein $R^{40}$ is optionally substituted with one or more, the same or different, $R^{42}$; and $R^{41}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, aryl sulfonyl, benzyl, benzoyl, carbocyclyl, aryl, or heterocyclyl, wherein $R^{41}$ is optionally substituted with one or more, the same or different, $R^{42}$; or $R^{41}$ is hydrogen or alkyl optionally substituted with one or more, the same or different, $R^{42}$;

$R^{42}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl.

In certain embodiments, $R^{40}$ is alkyl or alkyl substituted with one or more halogen such as trifluoromethyl.

In certain embodiments, the tetrahydroisoquinoline derivatives of formula I have formula IJ:

Formula IJ

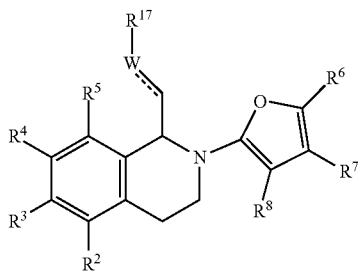

prodrugs or salts thereof, wherein:

W is O, S, NH, CH$_2$, provided ═ is a single bond or W is CH provided ═ is a double bond;

R$^2$, R$^3$, R$^4$, R$^5$, R$^6$, R$^7$, and R$^8$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^2$, R$^3$, R$^4$, R$^5$, R$^6$, R$^7$, and R$^8$ are optionally substituted with one or more, the same or different, R$^{20}$;

R$^{17}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{17}$ is optionally substituted with one or more, the same or different, R$^{20}$;

R$^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^{20}$ is optionally substituted with one or more, the same or different, R$^{21}$; and R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl.

In certain embodiments, the tetrahydroisoquinoline derivatives of formula I have formula IK:

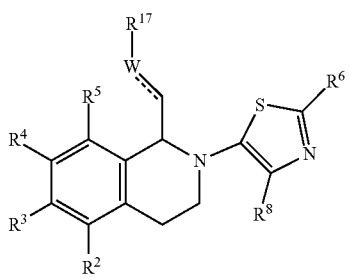

Formula IK

In certain embodiments, the tetrahydroisoquinoline derivatives of formula I have formula IL:

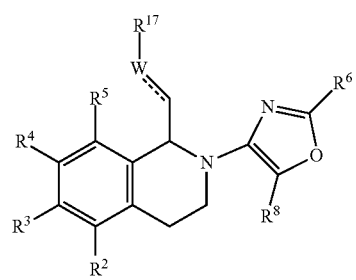

Formula IL prodrugs or salts thereof, wherein:

W is O, S, NH, CH$_2$, provided ═ is a single bond or W is CH provided ═ is a double bond;

R$^2$, R$^3$, R$^4$, R$^5$, R$^6$, and R$^8$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R$^2$, R$^3$, R$^4$, R$^5$, R$^6$, and R$^8$ are optionally substituted with one or more, the same or different, R$^{20}$;

R[17] is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R[17] is optionally substituted with one or more, the same or different, R[20];

R[20] is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkyl sulfonyl, aryl sulfonyl, carbocyclyl, aryl, or heterocyclyl, wherein R[20] is optionally substituted with one or more, the same or different, R[21]; and R[21] is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, isopropoxycarbonyl, tert-butoxycarbonyl, N-methylsulfamoyl, N-ethyl sulfamoyl, N,N-dim ethyl sulfamoyl, N,N-diethylsulfamoyl, N-methyl-N-ethylsulfamoyl, carbocyclyl, aryl, or heterocyclyl.

In certain embodiments, compounds of Formula I-IF are in a composition having Formula II-Formula IIF or Formula III-Formula IIIF respectively in greater than 55%, 65%, 75%, 85%, 95%, or 98% enantiomeric or diastereomeric excess, wherein Formula II
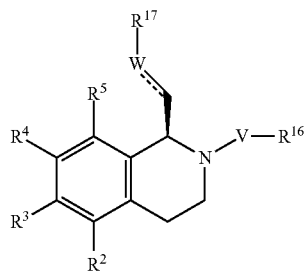

Formula IIA
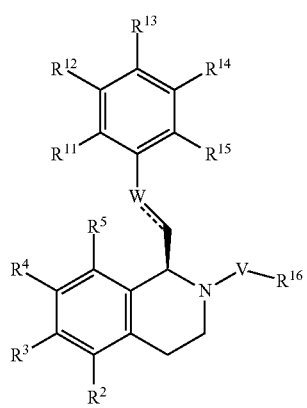

Formula IIB
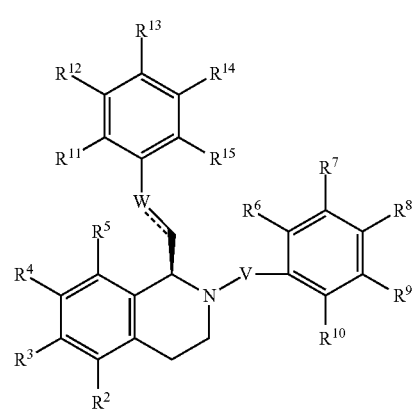

Formula IIC
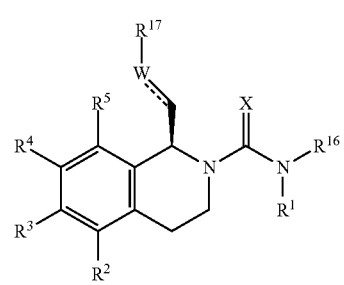

Formula IID
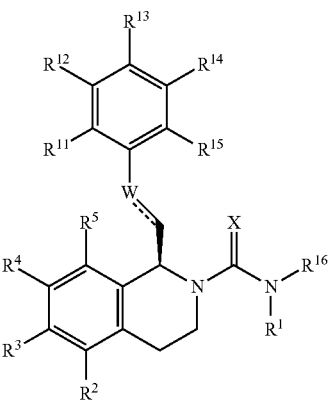

Formula IIE
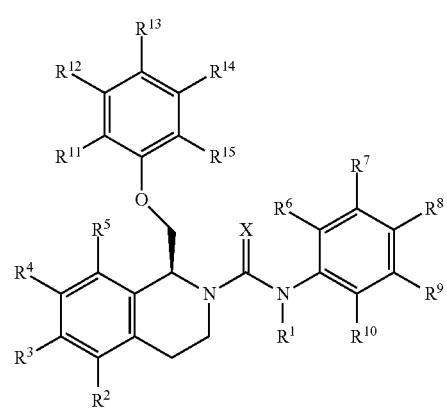

-continued
Formula IIG
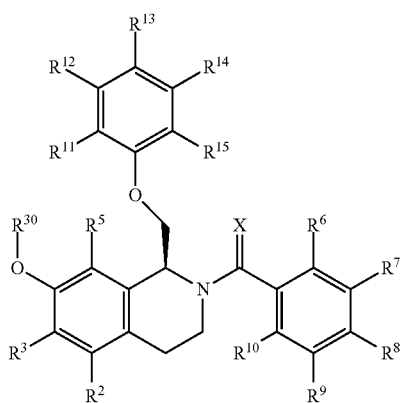
Formula IIH
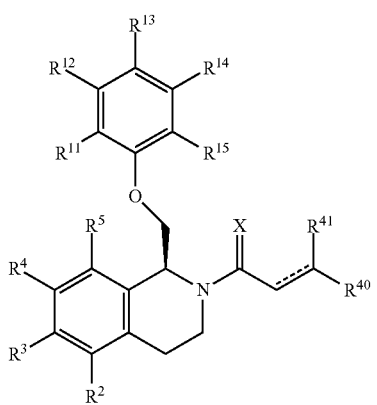
Formula IIF
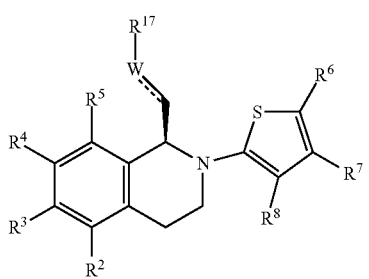
Formula IIJ
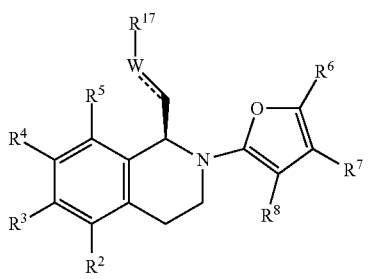
Formula IIK
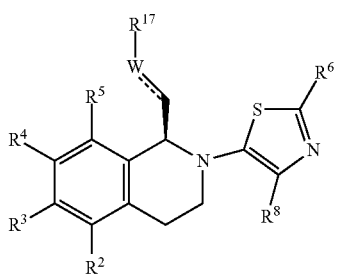
-continued
Formula IIL
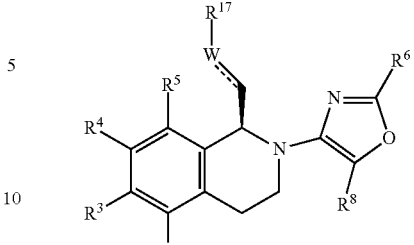
Formula III
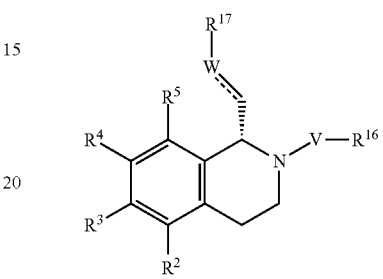
Formula IIIA
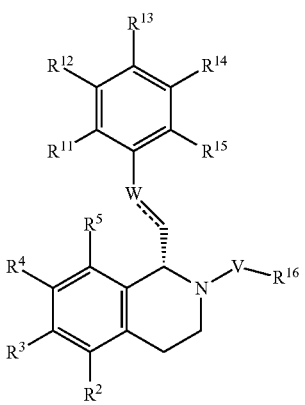
Formula IIIB
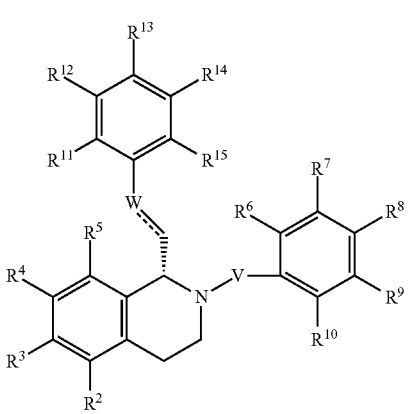
Formula IIIC
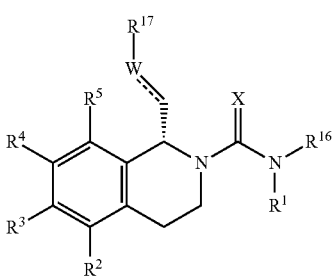

-continued

Formula IIID

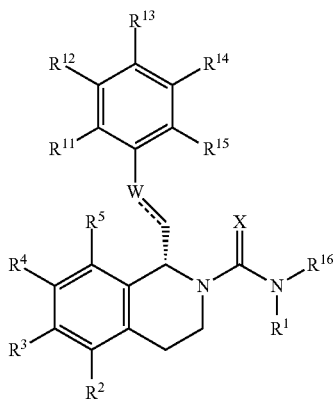

Formula IIIE

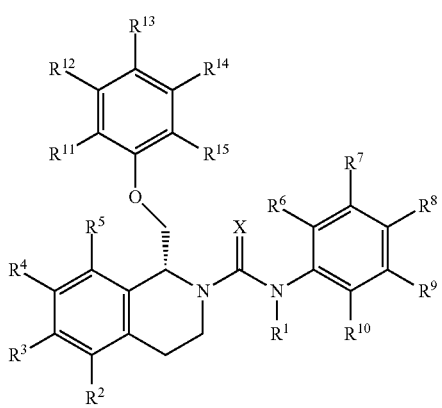

Formula IIIF

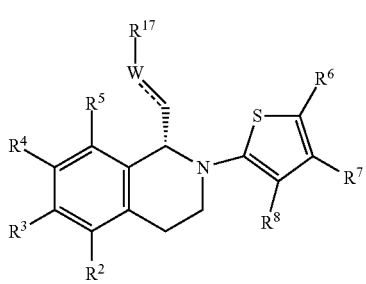

Formula IIIG

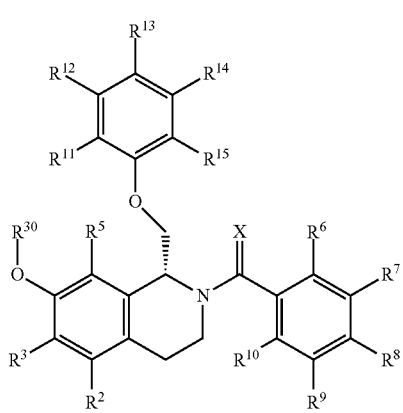

Formula IIIH

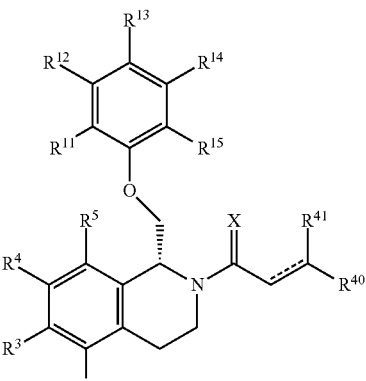

Formula IIIJ

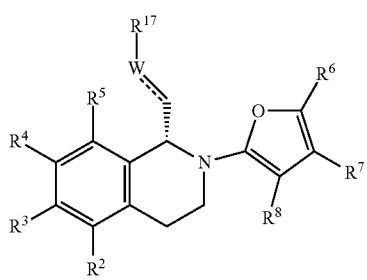

Formula IIK

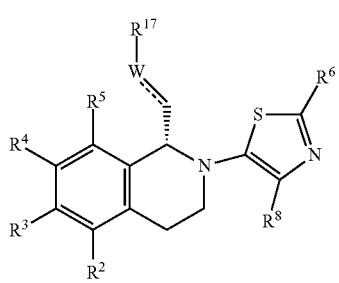

Formula IIL

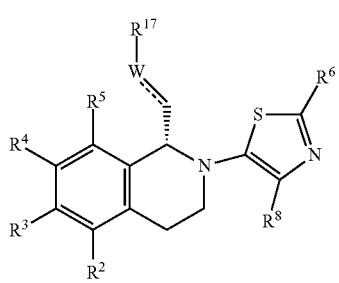

Methods of Use

NMDARs play an important role in processes such as synaptic plasticity, learning, and memory. Deficits in synaptic plasticity are thought to contribute to cognitive dysfunction in a wide range of indications, including Alzheimer's disease, autism, developmental delay, cognitive disability, schizophrenia, Parkinson's disease and other neurological diseases.

In certain embodiments, the disclosure relates to methods of treating or preventing a neurological disease, condition, or disorder comprising administering an effective amount of a tetrahydroisoquinoline compound or derivative disclosed herein to a subject in need thereof. In certain embodiments, the condition is depression, anxiety, schizophrenia, or bipolar disorder. In certain embodiments, the compound may be administered in combination with a second psychiatric medication, e.g., anti-depressant, anti-psychotic (typical or atypical), relaxant, chlorpromazine, haloperidol, perphenazine, fluphenazine, risperidone, olanzapine, quetiapine, ziprasidone, aripiprazole, paliperidone, etc.

In certain embodiments, the condition is a central nervous system (CNS) disorders such as those selected from Alzheimer's disease, Huntington's disease, and Amyotrophic Lateral Sclerosis (ALS). In certain embodiments, the disclosure relates to methods of improving learning or memory comprising administering an effective amount of a compound disclosed herein to a subject in need thereof.

In certain embodiments, the disclosure relates to methods of improving synaptic plasticity, learning, and memory by administering compounds disclosed herein to subject in need thereof. Deficits in synaptic plasticity are thought to contribute to cognitive dysfunction in a wide range of indications, including Alzheimer's disease, autism, developmental delay, cognitive disability, schizophrenia, Parkinson's disease and other neurological diseases. In certain embodiments, the disclosure relates to methods of treating or preventing Alzheimer's disease, autism or autism spectrum disorders, developmental delay, cognitive disability, schizophrenia, Parkinson's disease and other neurological diseases comprising administering compounds disclosed herein to a subject in need thereof.

Certain NMDARs contain a GluN1 subunit in addition to GluN2A-GluN2D subunits. Stimulation of one or more of the subunits are thought to be beneficial for the treatment of these conditions as well as other conditions dependent on synaptic plasticity such as motor retraining and rehabilitation after ischemic insult, traumatic brain injury, spinal cord injury, and conditions that involve impairment of movement, speech, vision, or other normal functions controlled by the brain. In certain embodiments, the disclosure relates to methods of managing, improving, treating or preventing motor retraining and rehabilitation after ischemic insult, traumatic brain injury, and conditions that involve in impairment of movement, speech, vision, or other functions controlled by the brain by administering an effective amount of a compound disclosed herein to a subject in need thereof.

In some embodiments, the disease or condition is depression, anxiety, epilepsy, post-traumatic stress disorder, dementia, diabetic neuropathy, peripheral neuropathy, or stroke.

In certain embodiments, the methods described herein include a method of treating or reducing the risk of disorders associated with neurological disorders, and neuropsychiatric disorders in a subject. Examples of neurological and neuropsychiatric disorders include depression, anxiety, Alzheimer's, CNS injuries, and the like. This method includes the steps of selecting a subject with or at risk of developing the neurological disorder or neuropsychiatric disorder and administering to the subject a therapeutically effective amount of a compound disclosed herein. The compound can be administered systemically (e.g., orally, parenterally (e.g. intravenously), intramuscularly, intreperitoneally, transdermally (e.g., by a patch), extracorporeally, topically, by inhalation, subcutaneously or the like), by administration into the central nervous system (e.g., into the brain (intracerebrally or intra ventricularly), spinal cord, or into the cerebrospinal fluid), or any combination thereof.

The subject in need thereof can be a patient diagnosed as suffering from depression or anxiety. These diseases and their diagnoses are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. In certain embodiments, the subject receiving a pharmaceutical composition containing a compound disclosed herein may be co-administered an antidepressant or anti-anxiolytic medication (in combination with as a single dose or separate medication). In certain embodiments, the patient has been diagnosed by a mental health professional (e.g., a psychiatrist) with an anxiety or depression disorder.

In certain embodiments, the disclosure contemplates the treatment of other mental disorders or conditions by administering effective amounts of compounds disclosed herein. contemplated mental disorders and conditions include, but are not limited to, acute stress disorder, adjustment disorder, adolescent antisocial behavior, adult antisocial behavior, age-related cognitive decline, agoraphobia, alcohol-related disorder, Alzheimer's, amnestic disorder, anorexia nervosa, anxiety, attention deficit disorder, attention deficit hyperactivity disorder, autophagia, bereavement, bibliomania, binge eating disorder, bipolar disorder, body dysmorphic disorder, bulimia nervosa, circadian rhythm sleep disorder, cocaine-addition, dysthymia, exhibitionism, gender identity disorder, Huntington's disease, hypochondria, multiple personality disorder, obsessive-compulsive disorder (OCD), obsessive-compulsive personality disorder (OCPD), posttraumatic stress disorder (PTSD), Rett syndrome, sadomasochism, and stuttering.

In certain embodiments, the disclosure contemplated the treatment of depression with compounds disclosed herein. Depression can be divided into several types. Major depression is the most severe form of depression characterized by a severe, persistent depressed mood and loss of interest or pleasure in normal activities accompanied by decreased energy, changes in sleep habits, restless behavior, difficulty concentrating, loss of appetite, feelings of guilt or hopelessness, and in severe cases, psychotic symptoms such as hallucinations, delusions, and even suicidal thoughts. An individual typically has a history (greater than 2 weeks) of persistent sad moods, loss of interest or pleasure in activities once enjoyed, and feelings of guilt or hopelessness, restless behavior, difficulty concentrating, and even suicidal thoughts in order to make a diagnosis of major depression. The Beck's Depression Scale Inventory, or other screen tests for depression, can be helpful in diagnosing depression.

Major depression can be treated with medications and/or counseling. Medications used include, but are not limited to, tricyclic antidepressants, monoamine oxidase inhibitors, selective serotonin re-uptake inhibitor (SSRIs), and some antidepressant drugs such as bupropion, reboxetine, trazodone, venlafaxine, and mitrazapine. Antipsychotic medications are typically administered to patients suffering from more severe forms of psychotic symptoms, such as delusions or hallucinations. Types of psychotherapy include interpersonal therapy, group therapy, and cognitive behavioral therapy.

Alternative therapeutic methods include the use of herbal products for management of chronic conditions, such as psychiatric disorders, including anxiety and depression.

A second form of depression is chronic low-grade depression, also known as dysthymia. Dysthymia is present most of the time for a period of two or more years wherein an individual experiences a decrease in his/her overall level of energy, appetite, and sleep, as well as has feelings of low self-esteem and hopelessness. These symptoms cause distress and the individual has difficulty functioning in everyday activities. These symptoms, however, are not as severe as those symptoms experienced in major depression. The cause and maintenance of these symptoms are typically due to one of the following problems: loss of a friend, substantial disappointment at work or home, prolonged or chronic illness, and alcohol or drug abuse. People who suffer from dysthymia are at an increased risk for episodes of major depression. This produces a behavioral pattern called "double depression" wherein the individual is mildly depressed most of the time, with periodic symptoms of major depression.

The least severe form of depression is a depressed mood. This is an emotional state dominated by feelings of sadness, gloominess, or emptiness, which may be associated with lack of energy. Depressed moods are usually temporary responses to an unhappy or stressful event.

In certain embodiments, the disclosure contemplated the treatment of autism spectrum disorders with compounds disclosed herein. Autism Spectrum Disorder, including Asperger Syndrome, is a spectrum of neurodevelopmental disorders characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities.

Administration of compounds disclosed herein may be when a child or infant shows the early signs of signs of autism spectrum disorder or other abnormal social or behavioral development, or about the time of developmental landmarks in infants or children that show early signs of autism spectrum disorder or other abnormal or behavioral development. A therapeutic intervention administered during this period could reset the developmental trajectory of the child preventing the acquisition of second order social impairments.

In certain embodiments, the disclosure contemplated the treatment of bipolar disorders with compounds disclosed herein. Bipolar disorder affects men and women equally and typically appears between the ages of 15 and 25. As opposed to unipolar major depression, the incidence of bipolar disorder does not vary widely around the world. The exact cause is unknown, but it is linked to areas of the brain which regulate mood, and has a strong genetic component. The American Psychiatric Association's "Diagnostic and Statistical Manual of Mental Disorders" describes two types of bipolar disorder, type I and type II. The type I (formerly known as manic depressive disorder), there has been at least one full manic episode. People with this type, however, may also experience episodes of major depression. In type II disorder, periods of "hypomania" involve more attenuate (less severe) manic symptoms that alternate with at least one major depressive episode. When the patients have an acute exacerbation, they may be in a manic state, depressed state, or mixed state. The manic phase is characterized by elevated mood, hyperactivity, over-involvement in activities, inflated self-esteem, a tendency to be easily distracted, or little need for sleep. In the depressive phase, there is loss of self-esteem, withdrawal, sadness, or a risk of suicide. Either the manic or the depressive episodes can predominate and produce a few mood swings, or the patterns of the mood swing may be cyclic. While in either phase, patients may abuse alcohol or other substances, which worsens the symptoms.

Methods for treating bipolar disorders differ depending upon the state of the patient. During an acute phase, hospitalization may be required to control the symptoms. In order to reduce the risk of switching into mania, hypomania or rapid cycling, a combination of a mood stabilizer (e.g. lithium; valproate) and/or antidepressants (e.g., bupropion) is utilized for controlling bipolar disorders. Even though lithium is often utilized in controlling manic and depressive relapses, careful medical supervision along with maintaining salt intake, avoiding non-steroidal anti-inflammatory drugs, and undertaking weight-reduction diets are typically performed in order to reduce possible renal failure. Valproate also is characterized by severe side effects including nausea, vomiting, anorexia, heartburn, and diarrhea. Finally, the use of antidepressants for suppressing bipolar disorder is typically monitored in order to achieve symptomatic remission. Therefore, safer therapeutic methods are needed in the art in order to reduce the severe side effects associated with current treatments of bipolar disorders.

In certain embodiments, the disclosure contemplated the treatment of cyclothymic disorders with compounds disclosed herein. Cyclothymic disorders are similar to bipolar disorders, but less extreme. Cyclothymic disorders are characterized by stages of mild mood changes with stages of mild depression and excitement (hypomania). The changes in mood are very irregular and abrupt, but the severity of the swings is less. Cyclothymia is treated like bipolar disorders, though often not as aggressively. Thus, safer treatments are needed in the art.

In certain embodiments, the disclosure contemplated the treatment of anxiety disorders with compounds disclosed herein. Anxiety disorders, panic attacks, and agoraphobia are conditions that occur as a manifestation of primary mood disorders such as depression. Anxiety is a feeling of apprehension or fear that lingers due to an individual's perception of persistent and unrelenting stress. Anxiety is typically accompanied by various physical symptoms including twitching, trembling, muscle tension, headaches, sweating (e.g., night sweats), dry mouth, or difficulty swallowing. Some people also report dizziness, a rapid or irregular heart rate, increased rate of respiration, diarrhea, or frequent need to urinate when they are anxious. Fatigue, irritable mood, sleeping difficulties, decreased concentration, sexual problems, or nightmares are also common. Some people are more sensitive to stress and are thus more likely to develop anxiety disorders. The propensity to succumb to anxiety attacks may be due to genetic predisposition or by previous (e.g. childhood) exposure to certain stresses.

Treatment of anxiety disorders includes diagnostic tests for blood differential and thyroid function as well as an electrocardiogram (EKG). If any worrisome physical signs or symptoms do not accompany the anxiety, a referral to a mental health care professional is recommended. Psychotherapy such as cognitive-behavior therapy (CBT) along with the medication benzodiazepines is typical in severe cases of anxiety. The use of addition to these treatments, use of antidepressants such as imipramine and the selective serotonin re-uptake inhibitor (SSRI) paroxetine are also contemplated.

In certain embodiments, the disclosure contemplated the treatment of panic disorders with compounds disclosed herein. Panic disorder, one of the anxiety disorders, is characterized by repeated and unexpected attacks of intense fear and anxiety. Panic attacks are usually not related to a particular situation and typically "peak" within ten minutes of their onset. The exact cause of panic disorder is unknown, but it is associated with multiple physiological factors. Panic disorder can occur with or without agoraphobia, but agoraphobia develops in one-third of cases. In certain embodiments, the disclosure contemplated the treatment of agoraphobia with compounds disclosed herein. Agoraphobia is a disorder characterized by avoidance of crowds, and open and public places, particularly if escape or assistance is not immediately available. The development of agoraphobia may involve learned behavior, since it reflects a fear of experiencing panic attacks in unprotected settings, and sometimes the association of panic attacks with areas where they have occurred.

Symptoms of panic disorder include shortness of breath, dizziness, palpitations, trembling, sweating, choking, nausea, numbness, chest pain, hot flashes or chills, fear of dying, fear of losing control, or fear of going insane. Symptoms of agoraphobia include anxiety about being in places where escape might be difficult, fear of being alone, fear of losing control in a public place, feeling of helplessness, or feelings of detachment.

In certain embodiments, the disclosure contemplated the treatment of attention deficit disorders (ADD) with compounds disclosed herein. Symptoms include developmentally inappropriate levels of attention, concentration, activity, distractibility, and impulsivity. There are three subcategories of attention deficit disorder: (1) attention deficit/hyperactivity disorder of the combined type; (2) attention deficit/hyperactivity disorder of the predominantly inattentive type; and (3) attention deficit/hyperactivity disorder of the predominantly hyperactive or impulsive type.

In certain embodiments, the disclosure contemplated the treatment of sleep disorders with compounds disclosed herein. A sleep disorder is a disruptive pattern of sleep that may include difficulty: falling or staying asleep, falling asleep at inappropriate times, excessive total sleep time, or abnormal behaviors associated with sleep. There are more than 100 different disorders of sleeping and waking. They can be grouped into four main categories: problems with staying and falling asleep (insomnia, e.g.), problems with staying awake (sleep state misperception, e.g.), problems with adhering to a regular sleep schedule (hypersomnias such as narcolepsy, e.g.), and sleep disruptive behaviors (sleep walking, e.g.). Both insomnia and sleep disruptive behaviors could be direct results of a patient suffering from a psychological disorder such as depression or anxiety.

In certain embodiments, the disclosure contemplated the treatment of insomnia with compounds disclosed herein. Insomnia includes any combination of difficulty with falling asleep, staying asleep, intermittent wakefulness, and early-morning awakening and can lead to the following disorders: psychophysiological, delayed sleep phase syndrome, hypnotic dependent disorder, and stimulant dependent sleep disorder. Episodes may be either transient (2-3 weeks) or chronic.

Sleep disruptive behaviors include sleep terror disorder, sleep walking or REM behavior disorders (a type of psychosis related to lack of REM sleep and lack of dreaming). Symptoms of sleep disruptive behaviors are depressed mood, anxiety, apathy, difficulty concentrating, irritability, daytime fatigue, drowsiness, and difficulty falling asleep.

In one aspect of the present disclosure, the psychiatric disorder to be treated is PTSD. PTSD is defined by DSM-IV as an anxiety disorder that an individual may develop following exposure to a traumatic event, and is characterized by (1) re-experiencing the traumatic event, such as recurrent nightmares, intrusive recollections of the event, flashbacks, physiological and psychological responses to internal or external cues relating to the event, etc; (2) persistent avoidance of thoughts, people or places associated with the event; (3) numbing of general responsiveness such as emotional detachment, restricted affect or loss of interest in activities; and (4) persistence of increased arousal such as exaggerated startle response, hypervigilance, irritability, or difficulty sleeping, etc.

In certain embodiments, the disclosure contemplates the treatment of schizophrenia with compounds disclosed herein. Schizophrenia is characterized by a breakdown of thought processes and by poor emotional responsiveness and is generally accompanied by social or occupational dysfunction. It is often described in terms of positive and negative symptoms. Positive symptoms can include delusions, disorganized speech and thinking, and tactile, auditory, visual, olfactory, and gustatory hallucinations, typically regarded as manifestations of psychosis. Negative symptoms are deficits of normal emotional responses or of other thought processes such as flat or blunted affect and emotion, poverty of speech, inability to experience pleasure, lack of desire to form relationships, and lack of motivation.

The onset of schizophrenia symptoms typically occurs in young adulthood. Diagnosis typically involves the patient meeting three criteria. The first is characteristic symptoms, in which the patient experiences two or more symptoms for more than one month including delusions, hallucinations, disorganized speech, catatonic behavior, and negative symptoms. The second is social or occupational dysfunction. The third is a significant duration, generally about six months.

A subject undergoing treatment with the methods of the disclosure may exhibits an improvement in one or more symptoms associated with the psychiatric disorder. For a description of the relevant symptoms, see, for example, the DSM-IV ((1994) Diagnostic and Statistical Manual of Mental Disorders (4th ed., American Psychiatric Association, Washington D.C.)), which is herein incorporated by reference. The efficacy of the methods of the disclosure can be assessed using any clinically recognized assessment method for measuring a reduction of one or more symptoms of the particular psychiatric disorder. Examples of such assessment methods are described in, for example, in Experiment 7 of PCT Application WO02/078629. "Alleviation of symptoms," in the context of a behavioral disorder, refers to improvement in the social or psychological function or health of a patient, as evaluated by any measure accepted in the art. Preferably, "alleviation of symptoms" is a clinically recognizable decrease in symptoms described in DSM-IV-TR (American Psychiatric Association, 2000). The psychosocial function of a patient may be evaluated using standard measures provided in DSM-IV-TR (American Psychiatric Association, 2001), such as the Global Assessment of Functioning Scale and the Social and Occupational Functioning Assessment Scale.

Formulations

In certain embodiments, the disclosure relates the use of compounds disclosed herein in the preparation of a medicament for uses disclosed herein. Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids, which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases, which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier, which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrug can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing at least one compound according to the disclosure with one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one compound of the disclosure, e.g., about 10, 25, 50, 100, 200, 300 or 400 mg per unit dosage.

The compounds can be administered by a variety of routes including oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers.

Certain of the above-mentioned polymers may further be crosslinked by way of standard techniques. The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

Experimental

Synthesis

Figure 1B:
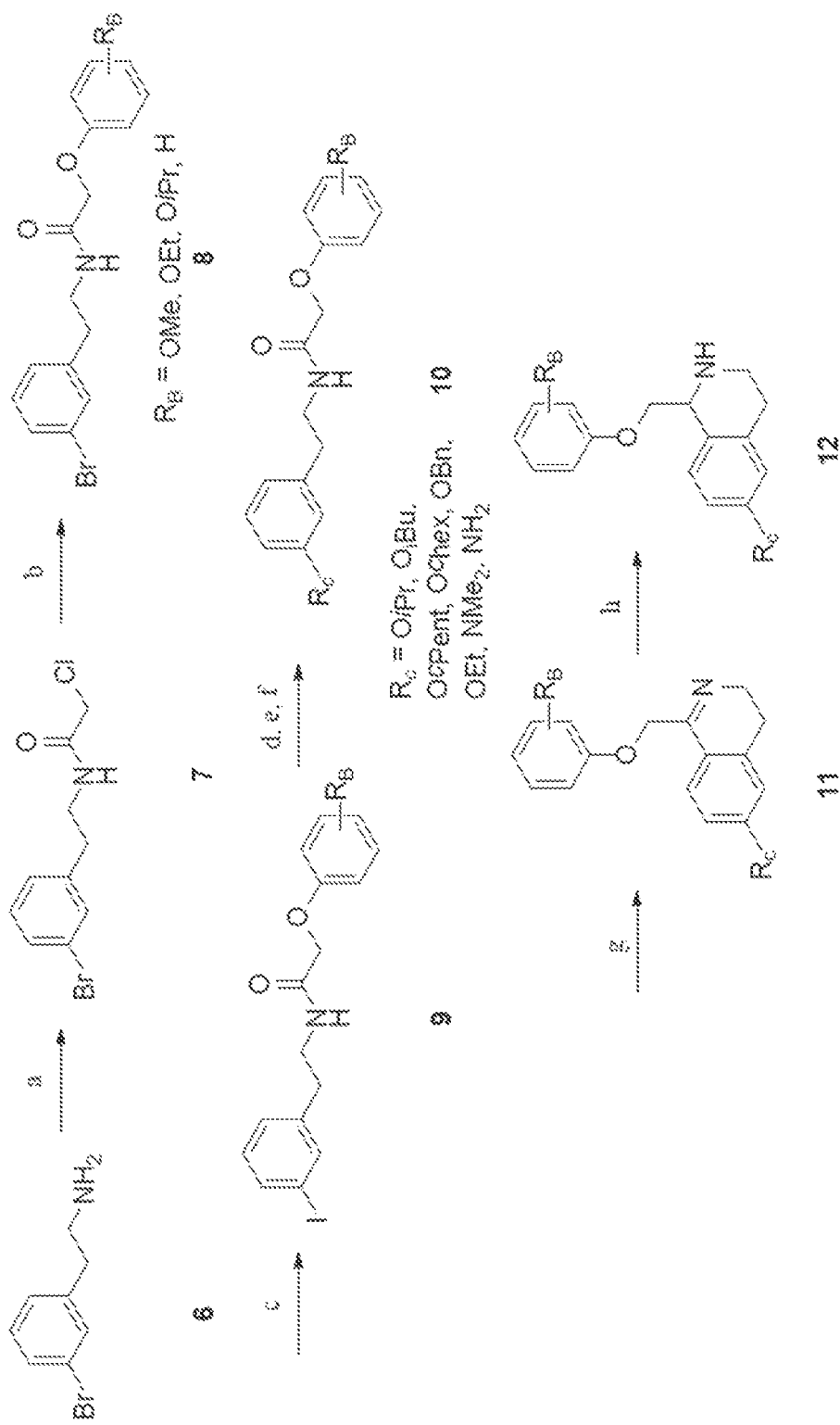
FIG. 1B illustrates the preparation of certain embodiments disclosed herein. a) chloroacetyl chloride, $Et_3N$, DCM, 3 h, 72%; b) substituted phenol, $Cs_2CO_3$, ACN, 20 h, 75-92%; c) NaI, CuI, N,N-dimethylethylenediamine, dioxane, sealed tube, 110° C., 24 h, 69-93%; d) substituted alcohol, CuI, 1,10-phen, sealed tube, 110° C., 19-38%; e) cyclic amines or cyclohexylamine, CuI, L-proline, $K_2CO_3$, DMSO, sealed tube, 80° C., 67-87%; f) $Cu(I)O_2$, $NH_4OH$, NMP, sealed tube, 80° C., 71%; g) $POCl_3$, toluene, reflux, 1-5 h; h) $NaBH_4$, MeOH, 20 h, 12-48%. In certain embodiments, $R_A$=alkyl, alkoxy, aryl and heteroaryl, Cl, Br, F, I, $CF_3$, OH, $NH_2$, $NR_2$, OMe, H, $NO_2$; $R_B$=alkyl, alkoxy, aryl and heteroaryl, OMe, OEt, OH, H, OiPr, $OCF_3$; $R_C$=alkyl, aryl and heteroaryl, alkoxy, such as OiPr, OiBu, OcPent, OcHex, $OCH(CH_2CH_3)_2$, OBn, as well as OH, $NMe_2$, NMeH, NMeiPr, $NiPr_2$, $NH_2$, NHiPr, N-morpholine, N-piperidine; Z=O, $CH_2$; X=CH, N.
Figure 2A:
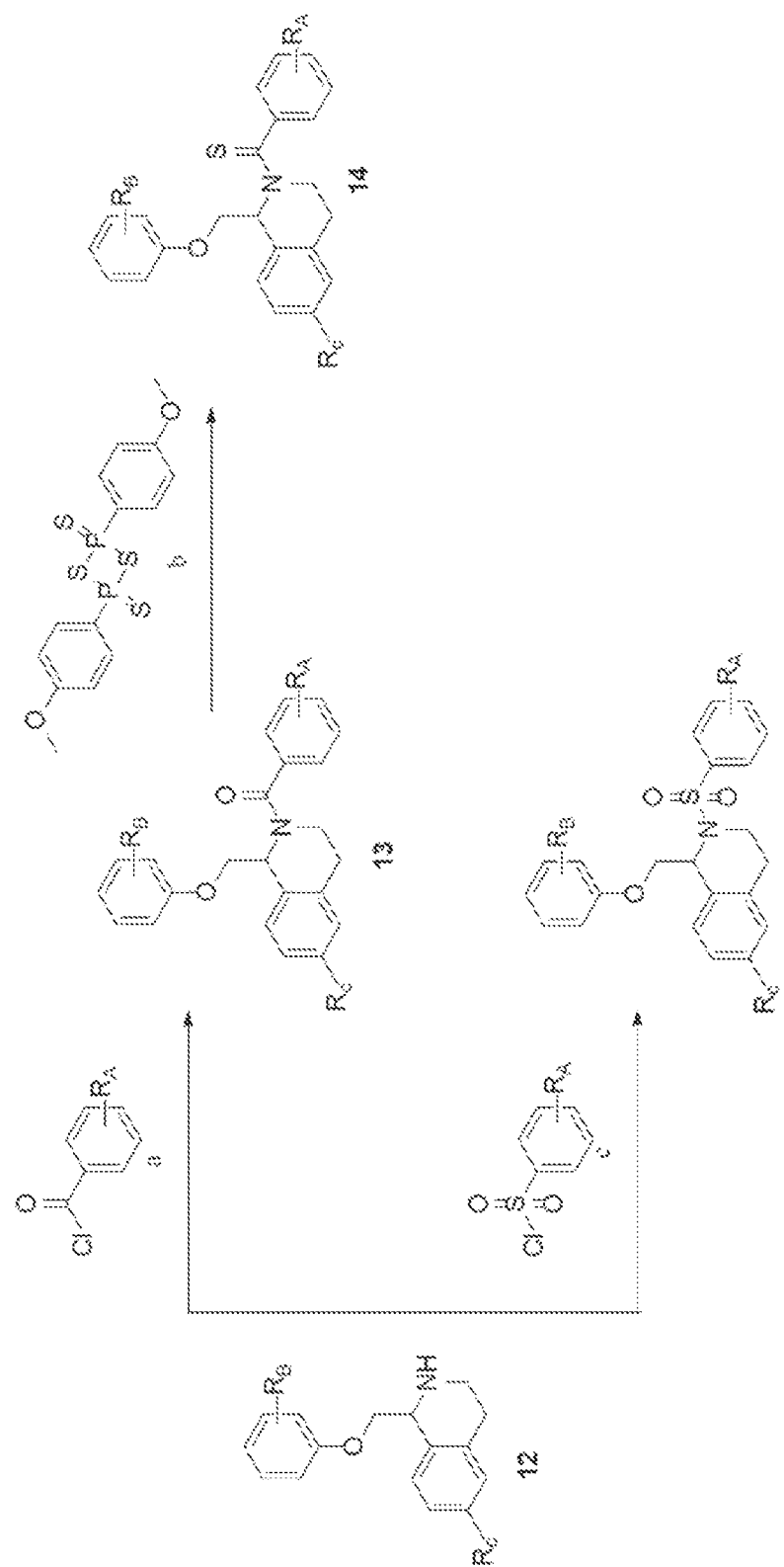
FIG. 2A illustrates the preparation of certain embodiments of this disclosure. a) $Et_3N$, DCM, 26-64%; b) toluene, reflux, 23-72%; c) $Et_3N$, DCM, 63%.
Figure 2B:
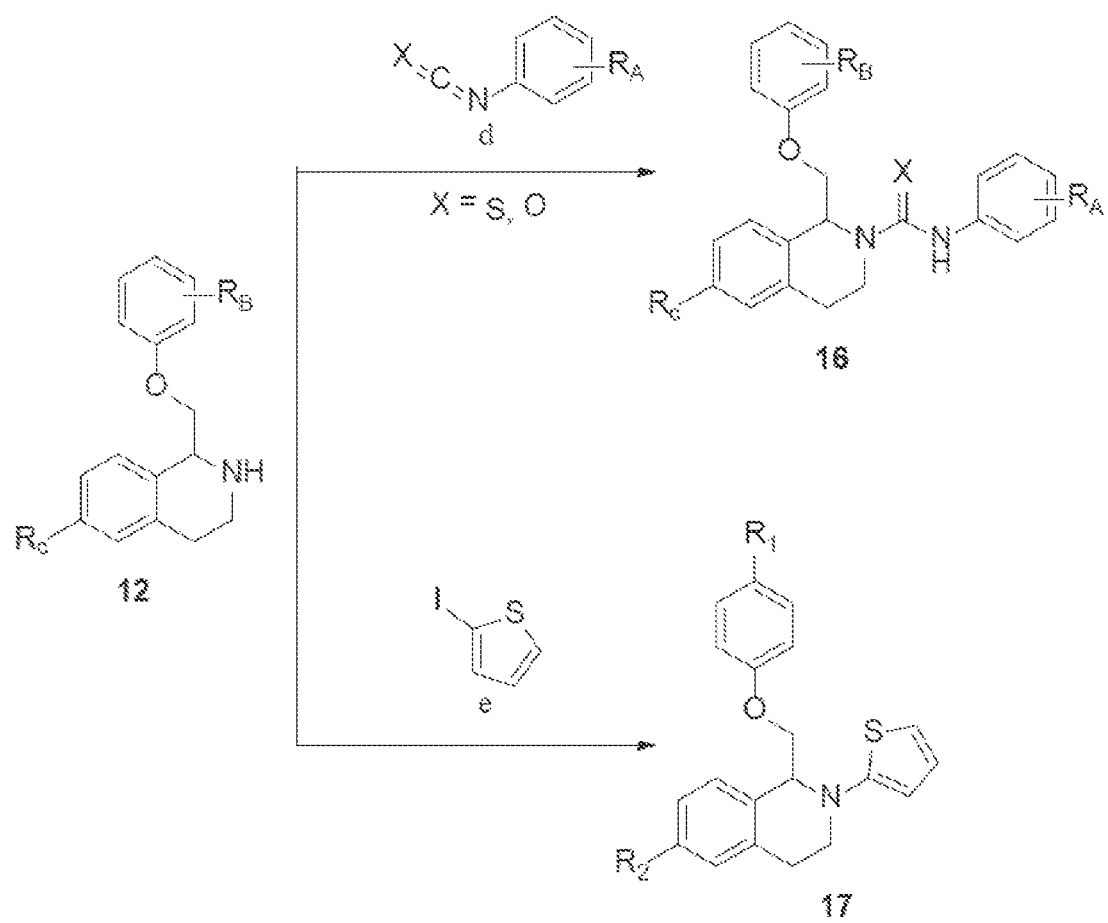
FIG. 2B illustrates the preparation of certain embodiments of this disclosure. d) THF, 61%; e) N, N-dimethylethanolamine, 10% Cu, 2.0 eq. $K_3PO_4.H_2O$.
Figure 3A:
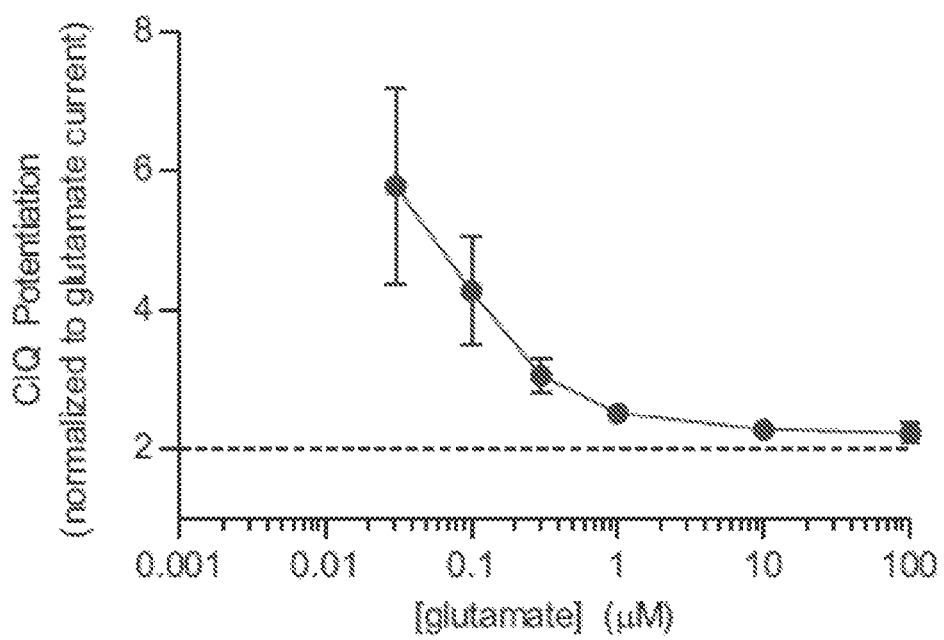
FIG. 3A shows data for TEVC recordings of the effect of CIQ (compound 1390) at different concentrations of glutamate.
Figure 3B:
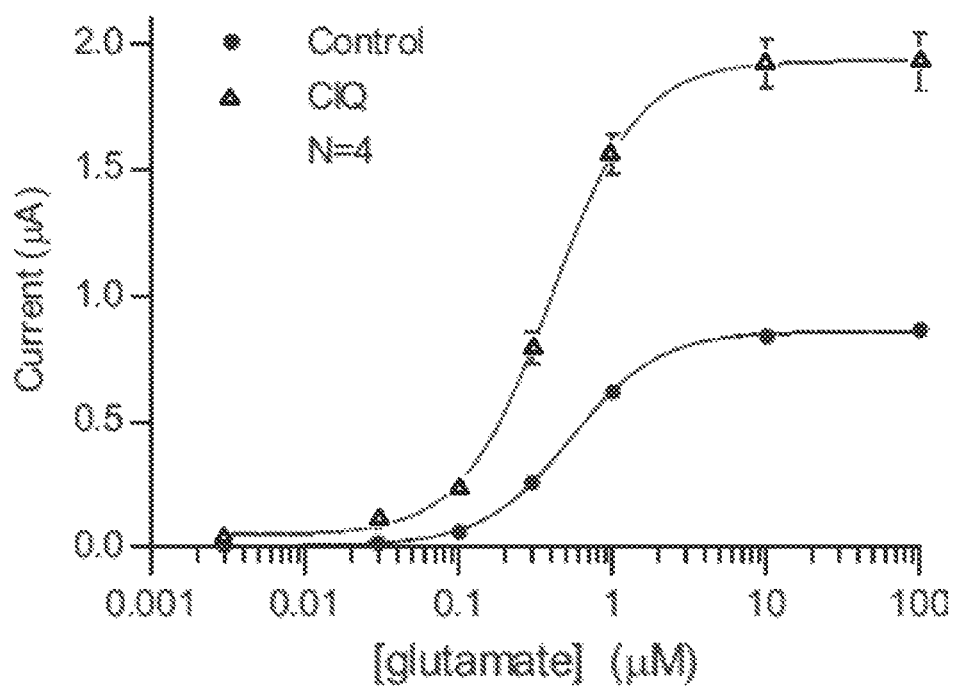
FIG. 3B shows data as in 3A re-plotted as a concentration effect curve for glutamate indicating that CIQ shifted the $EC_{50}$ (1.4 fold), which was enough to produce enhanced apparent potentiation at low agonist concentrations. CIQ, by enhancing potency, is believed to increase receptor occupancy in addition to enhancing open probability.
Figure 4A:
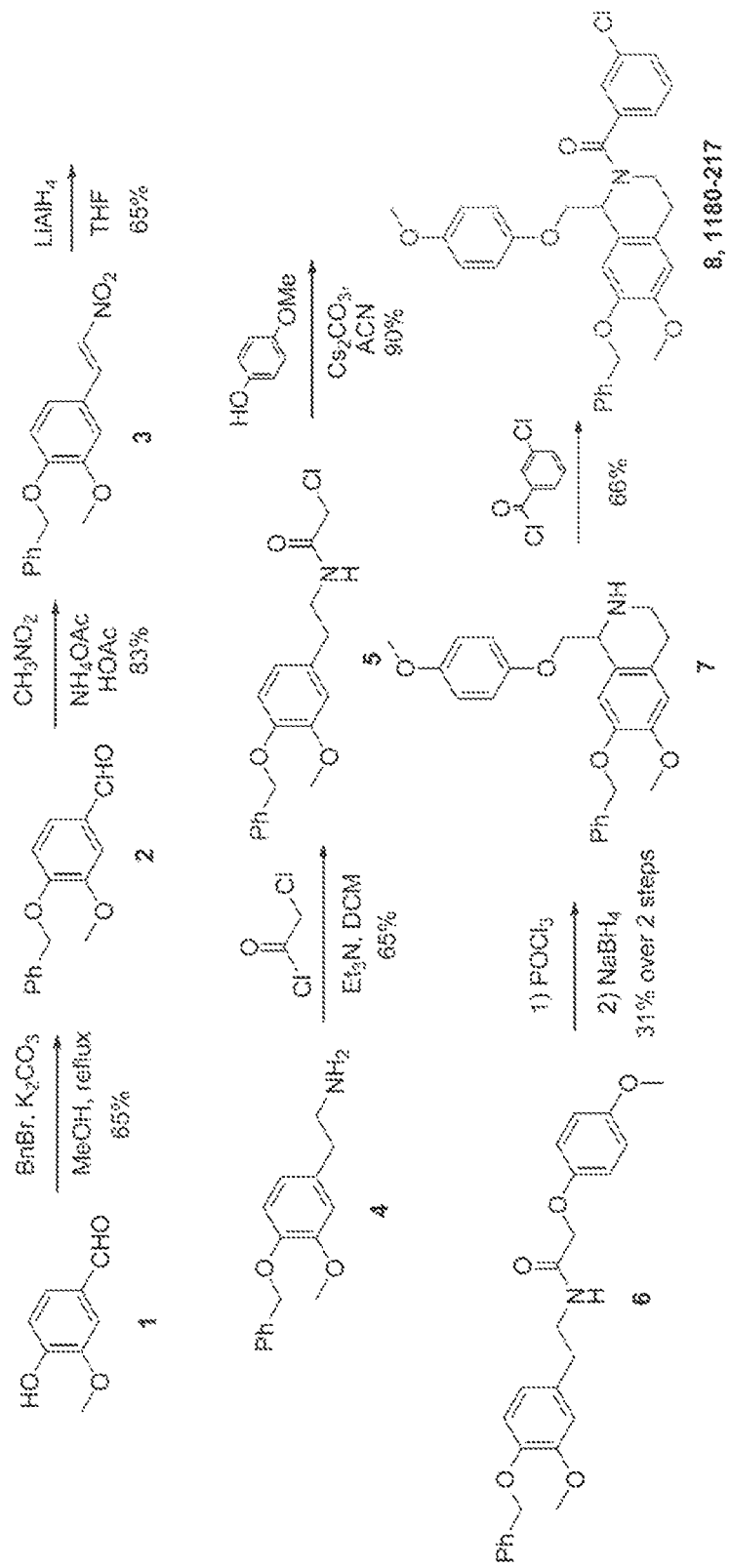
FIG. 4A illustrates certain embodiments disclosed herein.
Figure 4B:
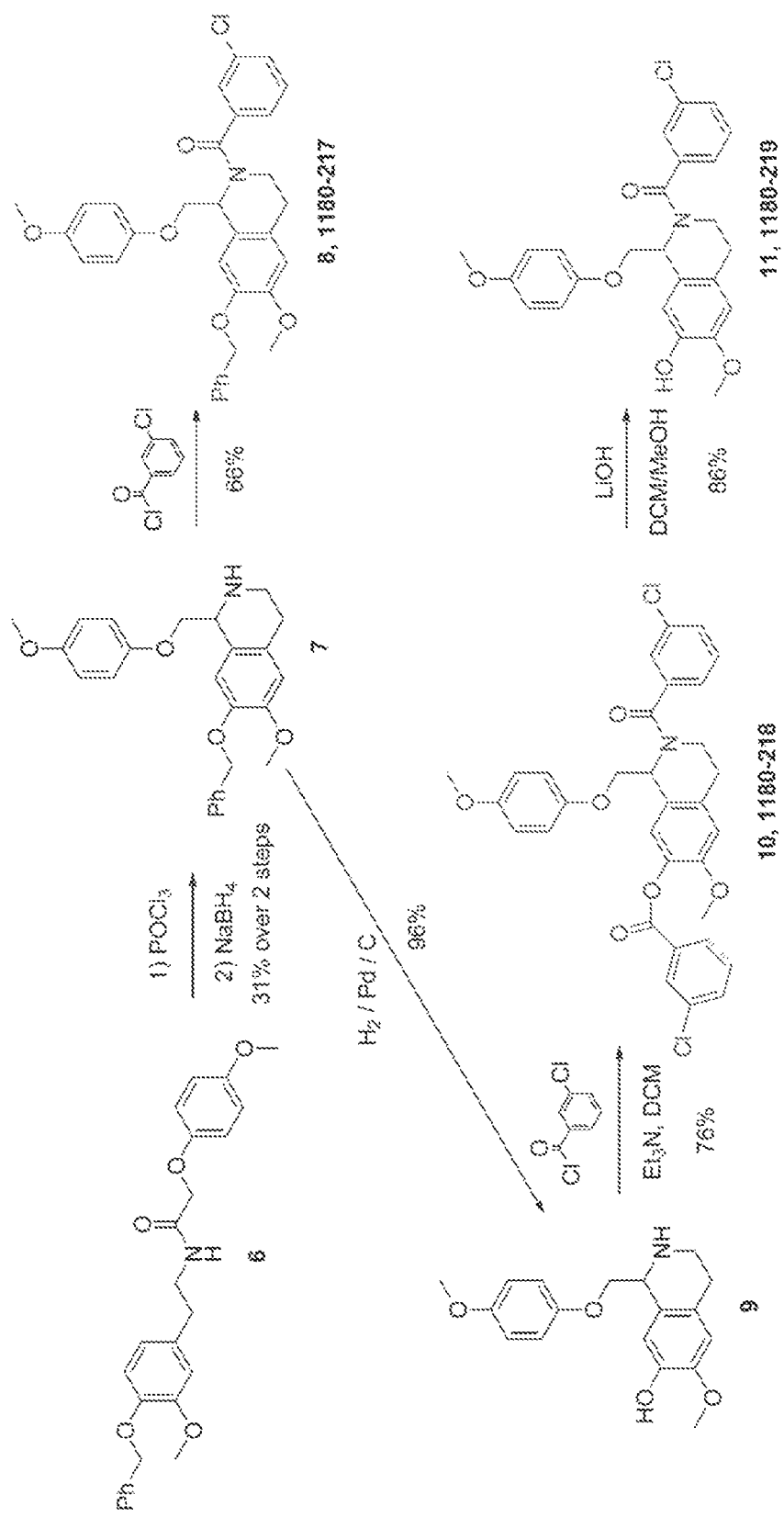
FIG. 4B illustrates the preparation of certain embodiments disclosed herein.
Figure 5:
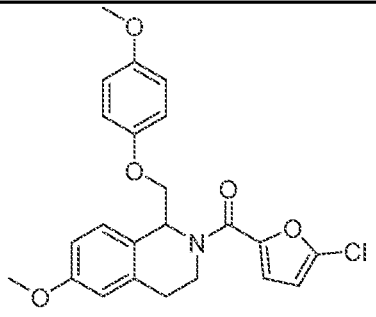
FIG. 5 illustrates certain embodiments disclosed herein. The compounds were prepared from the amine intermediate (See compound 12 in FIG. 1B) using the either a) the carboxylic acid chloride and triethylamine in DCM or b) from the same amine and carboxylic acid using HATU or EDCI and DIEA in DMF.
Figure 5:
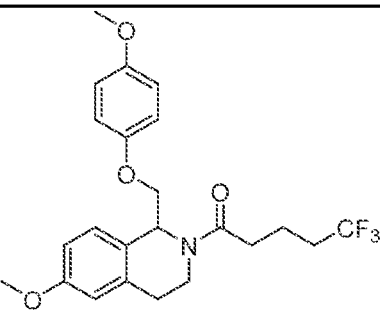
Figure 5:
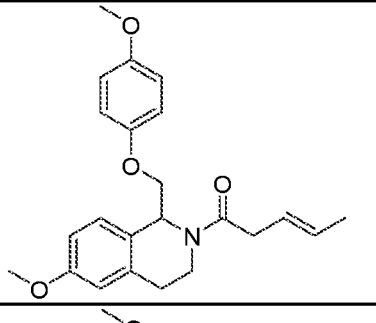
Figure 5:
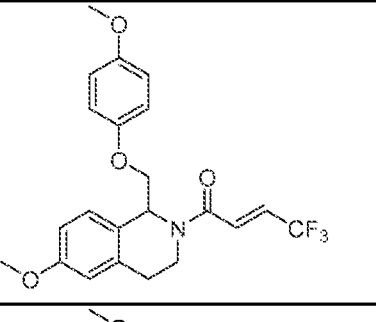
Figure 5:
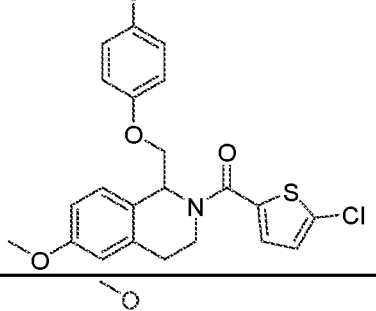
Figure 5:
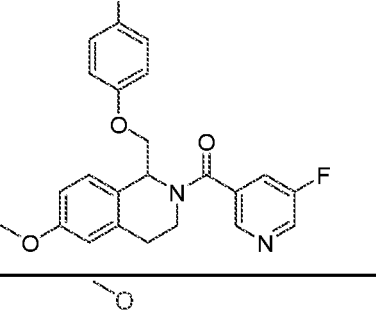
Figure 5:
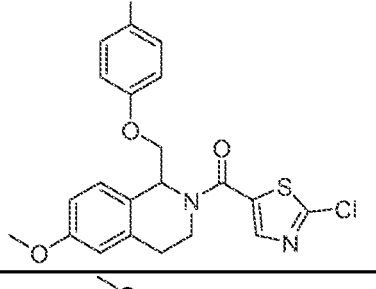
Figure 5:
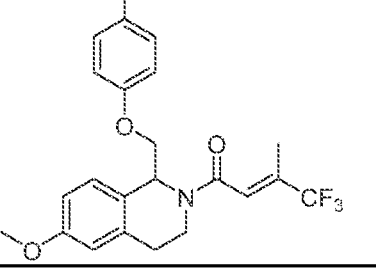
Figure 5:
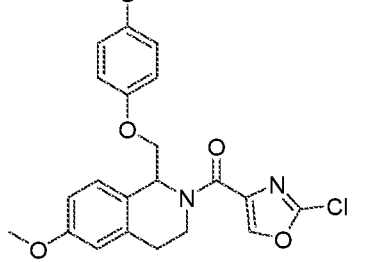

Certain compounds have been synthesized as in FIGS. 1, 2, and the schemes below. Additional compounds and data are shown below. Thioamide modifications in certain compounds have unexpectedly led to an improvement in potency.

TABLE 1

| 1180- | X | $R_1$ | GluN2A EC50 ($\mu$M)/Max % | GluN2B EC50 ($\mu$M)/Max % | GluN2C EC50 ($\mu$M)/Max % | GluN2D EC50 ($\mu$M)/Max % |
|---|---|---|---|---|---|---|
| 55 | O | Cl | NE | 4.5/193 | 1.8/266 | 2.9/243 |
| 163 | S | Cl | NE | 0.82/262 | 0.43/247 | 0.43/249 |

TABLE 1-continued

| 140 | O | F | 3.7/159 | 3.3/450 | 4.2/304 | 9.9/521 |
| 166 | S | F | 1.7/179 | 1.8/307 | 0.93/233 | 1.0/200 |

Additional thioamide enantiomer examples are shown below. The GluN2B activity typically resides in the (S)-(−)-enantiomer (with the exception of 1180-168). Some of the enantiomers are GluN2B-, GluN2C-, and GluN2D-NMDA potentiators with EC50 values below 0.50 μM at all three subunits ((S)-(−)-1180-163, (S)-(−)-1180-154, and (R)-(+)-1180-168). One is able to separate the amide-containing compounds via the AD-H semi-preparatory column, and then convert both enantiomers to the thioamide-containing counterparts.

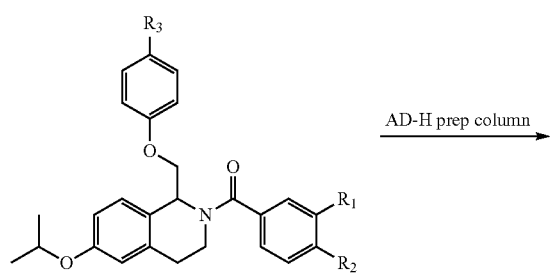

AD-H prep column

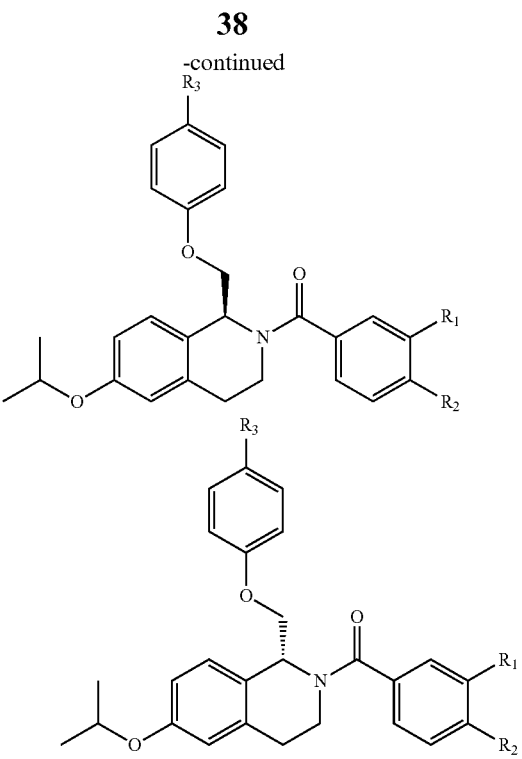

| Starting Material ID | Yield | R₁ | R₂ | Product ID |
|---|---|---|---|---|
| (S)-(−)-1180-55 | 65% | Cl | OMe | (S)-(−)-1180-163 |
| (R)-(+)-1180-55 | 49% | Cl | OMe | (R)-(+)-1180-163 |
| (S)-(−)-1180-87 | 56% | F | OEt | (S)-(−)-1180-154 |
| (R)-(+)-1180-87 | 65% | F | OEt | (R)-(+)-1180-154 |
| (S)-(−)-1180-92 | 50% | CF₃ | OEt | (S)-(−)-1180-168 |
| (R)-(+)-1180-92 | 48% | CF₃ | OEt | (R)-(+)-1180-168 |

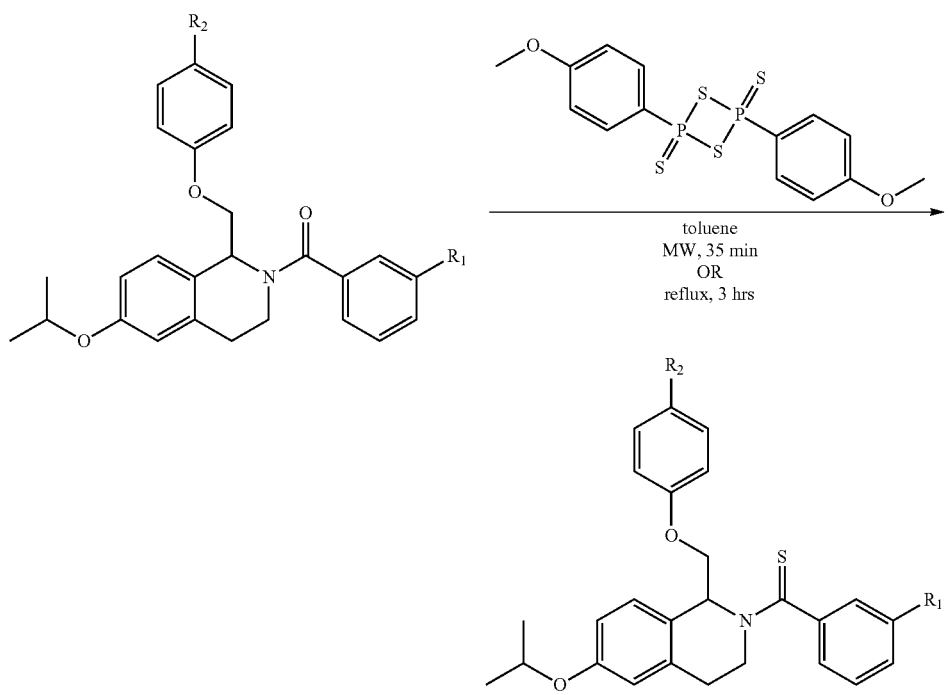

| Starting Material ID | Yield | R₁ | R₂ | Product ID |
|---|---|---|---|---|
| (S)-(−)-1180-55 | 65% | Cl | OMe | (S)-(−)-1180-163 |
| (R)-(+)-1180-55 | 49% | Cl | OMe | (R)-(+)-1180-163 |
| (S)-(−)-1180-87 | 56% | F | OEt | (S)-(−)-1180-154 |
| (R)-(+)-1180-87 | 65% | F | OEt | (R)-(+)-1180-154 |
| (S)-(−)-1180-92 | 50% | CF₃ | OEt | (S)-(−)-1180-168 |
| (R)-(+)-1180-92 | 48% | CF₃ | OEt | (R)-(+)-1180-168 |

TABLE 2

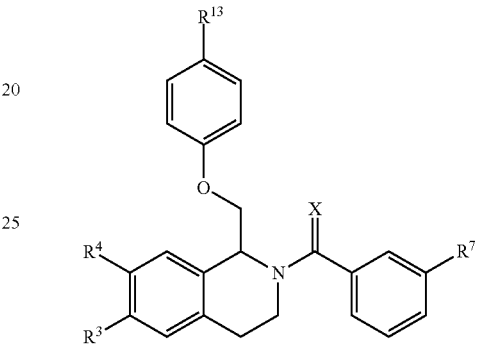

| 1180- | X | R₁ | R₂ | GluN2A EC50 (μM)/ Max % | GluN2B EC50 (μM)/ Max % | GluN2C EC50 (μM)/ Max % | GluN2D EC50 (μM)/ Max % |
|---|---|---|---|---|---|---|---|
| 83 | O | Cl | H | NE | 6.9/141 | 1.4/125 | NE |
| 149 | S | Cl | H | NE | 0.46/184 | 0.43/179 | 0.48/145 |
| 86 | O | Br | H | NE | 3.1/138 | 1.3/132 | NE |
| 156 | S | Br | H | NE | 0.44/187 | 0.36/161 | 0.13/130 |
| 144 | O | Cl | F | NE | 2.0/182 | 1.3/175 | 2.0/135 |
| 165 | S | Cl | F | 5.2/191 | 0.90/226 | 0.36/162 | 0.30/141 |

TABLE 3

Stereoselectivity of 1180-55 and 1180-163 enantiomers.

| | | I₁₀ μM/I_control (mean ± SEM, %) | | | EC₅₀ (max.) (μM %)ᵃ | | |
|---|---|---|---|---|---|---|---|
| | X | GluN2B | GluN2C | GluN2D | GluN2B | GluN2C | GluN2D |
| 1180-55 | O | 191 ± 6.5 | 231 ± 12 | 281 ± 3.1 | 5.0 (215%) | 2.6 (250%) | 4.3 (323%) |
| (R)-(+)-1180-55 | O | 150 ± 5.6 | 323 ± 17 | 345 ± 19 | 5.0 (167%) | 1.0 (342%) | 1.3 (384%) |
| (S)-(−)-1180-55 | O | 269 ± 21 | 361 ± 20 | 336 ± 19 | 5.2 (307%) | 3.9 (360%) | 4.5 (350%) |
| 1180-163 | S | 212 ± 2.2 | 272 ± 2.5 | 231 ± 2.5 | 0.11 (228%) | 0.32 (273%) | 0.14 (260%) |
| (R)-(+)-1180-163 | S | 121 ± 5.9 | 252 ± 8.4 | 215 ± 9.5 | — | 1.7 (252%) | 2.3 (255%) |
| (S)-(−)-1180-163 | S | 203 ± 11 | 302 ± 14 | 299 ± 12 | 0.28 (202%) | 0.50 (316%) | 0.50 (313%) |

Fitted EC50 values are shown to two significant digits when potentiation at 30 μM exceeded 120%; values in parentheses are the fitted maximum response as a percentage of the initial glutamate (100 μM) and glycine (30 μM) current. Data are from between 3-26 oocytes from 2-5 frogs for each compound and receptor tested.

| | | | | | EC50 (μM) or (μM %) | | |
|---|---|---|---|---|---|---|---|
| | R⁷ | R¹³ | R⁴ | R³ | X | GluN2B | GluN2C | GluN2D |
| 1180-264 | Cl | prop-2-yloxy | H | prop-2-yloxy | O | 4.6 | 127% at 30 mM | 101% at 30 mM |
| 1180-265 | Cl | prop-2-yloxy | H | prop-2-yloxy | S | 0.6 | 0.3 | 0.4 |

Other modifications favor GluN2B and GluN2C (Table 4), or yielded potentiators that favor GluN2C/D. (Table 8).

TABLE 4

| 1180- | X | R₁ | R₂ | GluN2A EC50 (μM)/ Max % | GluN2B EC50 (μM)/ Max % | GluN2C EC50 (μM)/ Max % | GluN2D EC50 (μM)/ Max % |
|---|---|---|---|---|---|---|---|
| 87 | O | F | H | NE | 7.7/152 | NE | NE |
| 154 | S | F | H | NE | 0.54/200 | 2.1/191 | 1.8/159 |

TABLE 4-continued

| 92 | O | CF$_3$ | H | NE | NE | 1.2/137 | NE |
| 168 | S | CF$_3$ | H | NE | 0.54/171 | 0.36/138 | NE |
| 103 | O | Cl | Cl | NE | 0.55/130 | 0.52/137 | NE |
| 155 | S | Cl | Cl | NE | 0.14/157 | 0.70/169 | NE |

TABLE 5

Stereoselectivity of 1180-87 and 1180-154 enantiomers.

| | X | I$_{30\ \mu M}$/I$_{control}$ (mean ± SEM, %) | | | EC$_{50}$ (max.) (μM %)$^a$ | | |
|---|---|---|---|---|---|---|---|
| | | GluN2B | GluN2C | GluN2D | GluN2B | GluN2C | GluN2D |
| 1180-87 | O | 151 ± 4.2 | 103 ± 2.2 | 91 ± 1.7 | 2.8 (152%) | — | — |
| (R)-(+)-1180-87 | O | 103 ± 1.2 | 103 ± 2.8 | 86 ± 2.1 | — | — | — |
| (S)-(−)-1180-87$^b$ | O | 195 ± 10 | 131 ± 5.4 | 119 ± 4.9 | 6.7 (206%) | 7.6 (132%) | — |
| 1180-154 | S | 184 ± 5.6 | 166 ± 10 | 154 ± 5.4 | 0.70 (190%) | 1.4 (145%) | 1.2 (153%) |
| (R)-(+)-1180-154 | S | 95 ± 1.6 | 58 ± 0.5 | 74 ± 3.2 | — | — | — |
| (S)-(−)-1180-154 | S | 206 ± 13 | 153 ± 11 | 185 ± 9.4 | 0.49 (213%) | 0.46 (163%) | 0.47 (190%) |

Fitted EC50 values are shown to two significant digits when potentiation at 30 μM exceeded 120%; values in parentheses are the fitted maximum response as a percentage of the initial glutamate (100 μM) and glycine (30 μM) current. Data are from between 3-26 oocytes from 2-5 frogs for each compound and receptor tested.

TABLE 6

Stereoselectivity of 1180-92 and 1180-168 enantiomers.

| | X | I$_{30\ \mu M}$/I$_{control}$ (mean ± SEM, %) | | | EC$_{50}$ (max.) (μM %)$^a$ | | |
|---|---|---|---|---|---|---|---|
| | | GluN2B | GluN2C | GluN2D | GluN2B | GluN2C | GluN2D |
| 1180-92 | O | 124 ± 7.0 | 129 ± 3.8 | 95 ± 8.6 | 2.5 (122%) | 1.4 (124%) | — |
| (R)-(+)-1180-92 | O | 75 ± 3.2 | 73 ± 4.1 | 75 ± 2.4 | — | — | — |
| (S)-(−)-1180-92 | O | 207 ± 7.8 | 132 ± 7.3 | 116 ± 5.2 | 1.9 (210%) | 1.2 (141%) | — |
| 1180-168 | S | 185 ± 14 | 139 ± 7.3 | 126 ± 4.8 | 1.0 (179%) | 0.33 (141%) | 0.45 (128%) |
| (R)-(+)-1180-168 | S | 156 ± 8.6 | 146 ± 8.1 | 157 ± 15 | 0.21 (173%) | 0.24 (182%) | 0.30 (160%) |
| (S)-(−)-1180-168 | S | 95 ± 1.8 | 87 ± 7.7 | 87 ± 1.5 | — | — | — |

Fitted EC$_{50}$ values are shown to two significant digits when potentiation at 30 μM exceeded 120%; values in parentheses are the fitted maximum response as a percentage of the initial glutamate (100 μM) and glycine (30 μM) current. Data are from between 3-26 oocytes from 2-5 frogs for each compound and receptor tested.

TABLE 7

Stereoselectivity of 1180-103 enantiomers.

| | X | I$_{30\ \mu M}$/I$_{control}$ (mean ± SEM, %) | | | EC$_{50}$ (max.) (μM %) | | |
|---|---|---|---|---|---|---|---|
| | | GluN2B | GluN2C | GluN2D | GluN2B | GluN2C | GluN2D |
| 1180-103 | O | 120 ± 4.4 | 134 ± 5.1 | 101 ± 4.2 | 1.4 (134%) | 0.65 (139%) | — |

TABLE 7-continued

| | | | | | | |
|---|---|---|---|---|---|---|
| (R)-(+)-1180-103 | O | 83 ± 4.9 | 92 ± 6.7 | 93 ± 8.0 | — | — |
| (S)-(−)-1180-103 | O | 153 ± 9.7 | 114 ± 6.8$^c$ | 102 ± 6.0$^c$ | 0.94 (163%) | — |

Fitted EC50 values are shown to two significant digits when potentiation at 30 μM exceeded 120%; values in parentheses are the fitted maximum response as a percentage of the initial glutamate (100 μM) and glycine (30 μM) current. Data are from between 3-26 oocytes from 2-5 frogs for each compound and receptor tested. Potentiation did not exceed 120% at 30 μM, but at 3 μM, the potentiation was greater than 120%.

TABLE 8

| 1180- | X | GluN2A EC50 (μM)/Max % | GluN2B EC50 (μM)/Max % | GluN2C EC50 (μM)/Max % | GluN2D EC50 (μM)/Max % |
|---|---|---|---|---|---|
| 104 | O | NE | 7.0/132 | 4.0/315 | 4.4/349 |
| 167 | S | NE | NE | 1.0/134 | 0.9/127 |

A sulfonamide and thiourea linker has been attached in place of the amide or thioamide, and both of these linker modifications yielded active compounds (Tables 9 and 10).

TABLE 9

| 1180- | GluN2A EC50 (μM)/Max % | GluN2B EC50 (μM)/Max % | GluN2C EC50 (μM)/Max % | GluN2D EC50 (μM)/Max % |
|---|---|---|---|---|
| 199 | NE | NE | 142% at 10 μM | NE |

TABLE 10

| 1180- | GluN2A EC50 (μM)/Max % | GluN2B EC50 (μM)/Max % | GluN2C EC50 (μM)/Max % | GluN2D EC50 (μM)/Max % |
|---|---|---|---|---|
| 210 | NE | NE | 0.30/173 | 0.74/174 |

Two-Electrode Voltage-Clamp (TEVC) Assay

Two-electrode voltage-clamp recordings were performed in Xenopus laevis oocytes (Ecocyte) expressing recombinant rat GluN1/GluN2A, GluN1/GluN2B, GluN1/GluN2C, GluN1/GluN2D. cRNA was transcribed in vitro (Ambion), diluted with nuclease free water, and injected at a ratio of 1:2 GluN1:GluN2 (5-10 ng total cRNA). The oocytes were kept in Barth's solution comprised of (in mM) 88 NaCl, 5 Tris-HCl, 2.4 NaHCO$_3$, 1 KCl, 0.84 MgSO$_4$, 0.41 CaCl$_2$, and 0.33 Ca(NO$_3$)$_2$ at pH 7.4 at 15-17° C. for two to five days before experiments. Oocytes were placed into a perfusion chamber and continually washed with recording solution containing (in mM) 90 NaCl, 1.0 KCl, 0.5 BaCl$_2$, 0.005 EDTA, and 10 HEPES at pH 7.4 (23° C.). Voltage clamp recordings were conducted at a holding potential of −40 mV. All compounds were made as 20 mM stock solutions in DMSO and dissolved to reach the final concentration in recording solution. Final DMSO content was 0.05-0.5% (vol/vol). Some oocytes expressing GluN1/GluN2A were pretreated with 50 mM BAPTA-AM for 10 minutes or injected with 50 mL of 2 mM K-BAPTA to prevent gradual run-up of the current response. EC50 values were determined by non-linear least squares fitting of $$\text{Response}=\text{Max}+(100-\text{Max})/(1+(\text{EC}_{50}/[\text{concentration}])N) \quad (1)$$

to concentration-response data from individual experiments normalized to the response in the absence of modulator (100%), where Max is the maximum percent potentiation, EC50 is the concentration that potentiates the response half-maximally and N is the Hill slope.

TABLE 11

| A-Ring | | | C-Ring | | EC₅₀ & Max Effect | | | |
|---|---|---|---|---|---|---|---|---|
| R₁ | R₂ | R₃ | R₄ | R₅ | 2C (μM) | Max (%) | 2D (μM) | Max (%) |
| H | H | H | OMe | OMe | 12.3 | 450 | 11.4 | 156 |
| Cl | H | H | OMe | OMe | 2.9 | 215 | 2.8 | 205 |
| Br | H | H | OMe | OMe | 0.9 | 145 | 2.2 | 188 |
| Br | H | H | Me | Me | 0.9 | 197 | 1.1 | 211 |
| Cl | H | H | OMe | H | 1.3 | 240 | 1.0 | 219 |
| Br | H | H | OBn | H | 0.31 | 257 | 0.27 | 219 |
| Cl | H | H | OCH₂Bn | H | 0.22 | 250 | 0.16 | 216 |
| Cl | H | H | SBn | H | 0.4 | 226 | 0.43 | 213 |
| Br | H | H | NMe₂ | H | 2.4 | 293 | 3.8 | 327 |

TABLE 12

Racemic and purified R and S enantiomers.

| | A-Ring | | | C-Ring | | EC₅₀ & Max Effect | | | |
|---|---|---|---|---|---|---|---|---|---|
| | R₁ | R₂ | R₃ | R₄ | R₅ | 2C (μM) | Max (%) | 2D (μM) | Max (%) |
| 1390 (CIQ) | Cl | H | H | OMe | OMe | 2.9 | 215 | 2.8 | 205 |
| S-1390 | Cl | H | H | OMe | OMe | 6.1 | 275 | 9.0 | 299 |
| R-1390 | Cl | H | H | OMe | OMe | Inactive | — | Inactive | — |

TABLE 13

| | A-Ring | B-Ring | C-Ring | | | EC₅₀ & Max Effect | | | |
|---|---|---|---|---|---|---|---|---|---|
| | R₁ | R₂ | R₃ | R₄ | X | 2C (μM) | Max (%) | 2D (μM) | Max (%) |
| 1390 (CIQ) | Cl | OMe | OMe | OMe | O | 2.9 | 215 | 2.8 | 205 |
| 1180-161 | Cl | OMe | OMe | OMe | S | Inactive | — | Inactive | — |
| 1391 | Br | OMe | OMe | OMe | O | 0.90 | 145 | 2.2 | 188 |
| 1180-157 | Br | OMe | OMe | OMe | S | Inactive | — | Inactive | — |
| 1180-55 | Cl | OMe | O/Pr | H | O | 1.8 | 266 | 2.9 | 243 |
| 1180-163 | Cl | OMe | O/Pr | H | S | 0.43 | 247 | 0.43 | 249 |
| 1180-112 | F | OEt | OcPent | H | O | 4.1 | 170 | 4.2 | 157 |
| 1180-162 | F | OEt | OcPent | H | S | 0.26 | 218 | 0.39 | 295 |

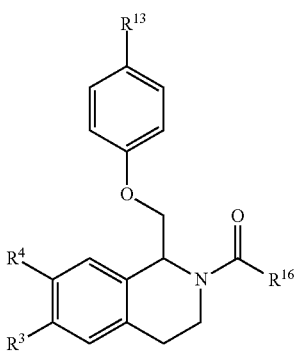

| | R[16] | R[13] | R[4] | R[3] | EC50 (μM) or (μM %) | | |
|---|---|---|---|---|---|---|---|
| | | | | | GluN2B | GluN2C | GluN2D |
| 1180-234 | 5-chlorofuran-2-yl | OMe | H | OMe | 107% at 30 μM | 2.6 | 5.5 |
| 1180-239 | (5-chlorothiophen-2-yl) | OMe | H | OMe | 1.6 | 0.9 | 1 |
| 1180-241 | 2-chlorothiazol-5-yl | OMe | H | OMe | 88% at 30 μM | 114% at 30 μM | 131% at 30 μM |
| 1180-247 | 2-chlorooxazol-4-yl | OMe | H | OMe | 99% at 30 μM | 65 | 223% at 100 μM |
| 1180-235 | but-2-en-1-yl | OMe | H | OMe | 103% at 30 mM | 184% at 30 mM | 222% at 30 mM |
| 1180-240 | ethoxymethyl | OMe | H | OMe | 100% at 30 mM | 115% at 30 mM | 114% at 30 mM |
| 1180-251 | 2-chlorovin-1-yl | OMe | H | OMe | 96% at 30 mM | 99% at 30 mM | 88% at 30 mM |
| 1180-252 | 4,4,4-trifluorobut-1-yl | OMe | H | OMe | 96% at 30 mM | 11 | 14 |
| 1180-253 | 3,3,3-trifluoroprop-1-en-1-yl | OMe | H | OMe | 101% at 30 mM | 7 | 9 |
| 1180-255 | 3,3,3-trifluoro-2-methylprop-1-en-1-yl | OMe | H | OMe | 99% at 30 mM | 15 | 23 |
| 1180-263 | 3,3,3-trifluoro-2-methylprop-1-en-1-yl | OEt | H | OiPr | 145% at 30 mM | 165% at 30 mM | 146% at 30 mM |
| 1180-328 | 3,3,3-trifluoroprop-1-en-1-yl | OMe | hydroxyl | OMe | 100 at 30 mM | 109 at 30 mM | 120 at 30 mM |
| 1180-330 | 3,3,3-trifluoroprop-1-en-1-yl | OMe | (3-chloro benzoyl)oxy | OMe | 95 at 30 mM | 102 at 30 mM | 96 at 30 mM |

The invention claimed is:

1. A compound having formula I

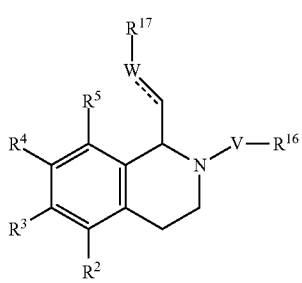

Formula I or a salt thereof, wherein:

V is C=S, C=O, or —SO$_2$;

W is O, S, NH, CH$_2$, provided ═ is a single bond or W is CH provided ═ is a double bond;

R$^2$ and R$^5$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^2$ and R$^5$ are optionally substituted with one or more, the same or different, R$^{20}$;

R$^3$ is selected from (C$_{2-4}$)alkoxy, isopropoxy, (C$_{3-6}$)cycloalkyloxy, cyclopentyloxy, alkylamino, dialkylamino, morpholinyl, and piperidinyl;

R$^4$ is hydrogen;

R$^{16}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{16}$ is optionally substituted with one or more, the same or different, R$^{20}$;

R$^{17}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{17}$ is optionally substituted with one or more, the same or different, R$^{20}$;

R$^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein R$^{20}$ is optionally substituted with one or more, the same or different, R$^{21}$; and R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1 wherein $R^3$ is isopropoxy or cyclopentyloxy optionally substituted with one or more, the same or different, $R^{20}$.

3. The compound of claim 1, wherein V is C=S or $SO_2$.

4. The compound of claim 1, wherein $R^{16}$ is a five-membered heterocyclyl, thiophenyl, furanyl, thiazolyl, or oxazolyl wherein $R^{16}$ is optionally substituted with one or more, the same or different, $R^{20}$.

5. A composition comprising a compound of formula II or III or a salt thereof, in greater than 55% enantiomeric excess, wherein

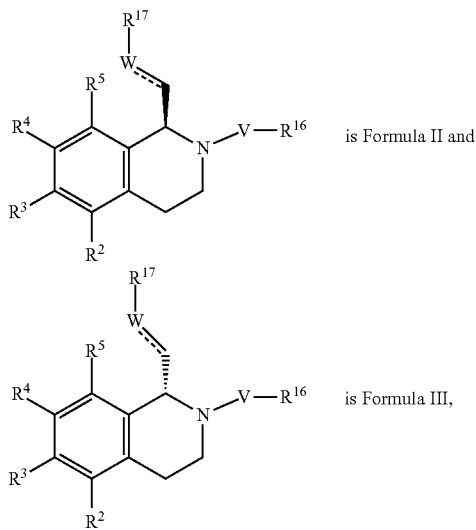

is Formula II and is Formula III,

V is C=S, C=O, or —$SO_2$;

W is O, S, NH, $CH_2$, provided ⸺ is a single bond or W is CH provided ⸺ is a double bond;

$R^2$ and $R^5$ are each, individually and independently, hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^2$ and $R^5$ are optionally substituted with one or more, the same or different, $R^{20}$;

$R^3$ is selected from ($C_{2-4}$)alkoxy, isopropoxy, ($C_{3-6}$)cycloalkyloxy, cyclopentyloxy, alkylamino, dialkylamino, morpholinyl, and piperidinyl;

$R^4$ is hydrogen;

$R^{16}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^{16}$ is optionally substituted with one or more, the same or different, $R^{20}$;

$R^{17}$ is hydrogen, alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^{17}$ is optionally substituted with one or more, the same or different, $R^{20}$;

$R^{20}$ is alkyl, halogen, nitro, cyano, hydroxy, amino, mercapto, formyl, carboxy, carbamoyl, alkoxy, hydroxyalkyl, alkylthio, thioalkyl, alkylamino, aminoalkyl, (alkyl)$_2$amino, alkanoyl, alkoxycarbonyl, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, isopropoxy, tert-butoxy, hydoxymethyl, hydroxyethyl, thiomethyl, thioethyl, aminomethyl, aminoethyl, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, isopropoxycarbonyl, tert-butoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

6. The composition of claim 5, wherein the compound is (R)-(1-((4-ethoxyphenoxy)methyl)-6-isopropoxy-3,4-dihydroisoquinolin-2(1H)-yl)(3-(trifluoromethyl)phenyl)methanethione, or a salt thereof.

7. The composition of claim 5, wherein the compound is (S)-(1-((4-ethoxyphenoxy)methyl)-6-isopropoxy-3,4-dihydroisoquinolin-2(1H)-yl)(3-fluorophenyl)methanethione, or a salt thereof.

8. A pharmaceutical composition comprising a compound as in claim 1 and a pharmaceutically acceptable excipient.

9. A method of treating depression or schizophrenia comprising administering an effective amount of a compound of claim 1 to a subject in need thereof.

10. A method of improving learning or memory comprising administering an effective amount of a compound of claim 1 to a subject in need thereof.

11. A method of improving recovery and retraining after a CNS injury comprising administering an effective amount of a compound of claim 1 to a subject in need thereof.

12. The method of claim 11, wherein the CNS injury is traumatic brain injury, stroke, hypoxia, cognitive deficits following coronary artery bypass grafting, and spinal cord injury.

* * * * *